US012608862B2

(12) United States Patent
Shen et al.

(10) Patent No.: US 12,608,862 B2
(45) Date of Patent: Apr. 21, 2026

(54) PRIOR-INCORPORATED DEEP LEARNING FRAMEWORK FOR SPARSE IMAGE RECONSTRUCTION BY USING GEOMETRY AND PHYSICS PRIORS FROM IMAGING SYSTEM

(71) Applicant: The Board of Trustees of the Leland Stanford Junior University, Stanford, CA (US)

(72) Inventors: Liyue Shen, Cambridge, MA (US); Lei Xing, Palo Alto, CA (US); Lianli Liu, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 329 days.

(21) Appl. No.: 18/196,894

(22) Filed: May 12, 2023

(65) Prior Publication Data

US 2023/0368438 A1    Nov. 16, 2023

Related U.S. Application Data

(60) Provisional application No. 63/341,239, filed on May 12, 2022.

(51) Int. Cl.
*G06T 12/10* (2026.01)
*G16H 30/40* (2018.01)

(52) U.S. Cl.
CPC ............ *G06T 12/10* (2026.01); *G16H 30/40* (2018.01); *G06T 2207/10072* (2013.01); *G06T 2207/20084* (2013.01)

(58) Field of Classification Search
CPC ......... G06T 11/005; G06T 2207/10072; G06T 2207/20084; G06T 11/006; G16H 30/40
See application file for complete search history.

(56) References Cited

U.S. PATENT DOCUMENTS

2019/0261945 A1 *  8/2019  Funka-Lea ............ G06T 15/205
2020/0034948 A1 *  1/2020  Park ......................... G06T 5/70
2021/0074036 A1 *  3/2021  Fuchs .................... A61B 6/032

OTHER PUBLICATIONS

Zhang, Zhicheng & Liang, Xiaokun & Dong, Xu & Xie, Yaoqin & Cao, Guohua. (2018). A Sparse-View CT Reconstruction Method Based on Combination of DenseNet and Deconvolution. IEEE Transactions on Medical Imaging. 37. 1-1. 10.1109/TMI.2018. 2823338. (Year: 2018).*

(Continued)

*Primary Examiner* — Abhishek Sarma
(74) *Attorney, Agent, or Firm* — LUMEN PATENT FIRM

(57)    ABSTRACT

A method for medical imaging performs a sparse-sampled tomographic imaging acquisition by an imaging system to produce acquired sparse imaging samples; synthesizes by a first deep learning network unacquired imaging samples from the acquired imaging samples to produce complete imaging samples comprising both the acquired imaging samples and unacquired imaging samples; transforms by a physics module the complete imaging samples to image space data based on physics and geometry priors of the imaging system; and performs image refinement by a second deep learning network to produce tomographic images from the image space data. The physics and geometry priors of the imaging system comprise geometric priors of a physical imaging model of the imaging system, and prior geometric relationships between the sample and image data domains.

8 Claims, 13 Drawing Sheets

(56)            References Cited

OTHER PUBLICATIONS

Novel-view X-ray projection synthesis through geometry-integrated deep learning, Medical Image Analysis vol. 77, Apr. 2022, 102372.
Shen, et al. Real time volumetric MRI for 3D motion tracking via geometry-informed deep learning. Med Phys. Jun. 29, 2022; 49: 6110-6119.
Shen et al., A Geometry-Informed Deep Learning Framework for Ultra-Sparse 3D Tomographic Image Reconstruction. May 25, 2021 arXiv:2105.11692 [cs.CV].
Huang, et al., "Multimodal unsupervised image-to-image translation," Aug. 14, 2018, arXiv:1804.04732v2 [cs.CV].
Shen et al., "Multi-Domain Image Completion for Random Missing Input Data," Jul. 10, 2020, arXiv:2007.05534v1 [cs.CV].

* cited by examiner

Geometry-Preserving
3D Images

Final 3D Images

PRIOR-INCORPORATED DEEP LEARNING FRAMEWORK FOR SPARSE IMAGE RECONSTRUCTION BY USING GEOMETRY AND PHYSICS PRIORS FROM IMAGING SYSTEM

CROSS-REFERENCE TO RELATED APPLICATIONS

This application claims priority from U.S. Provisional Patent Application 63/341,239 filed May 12, 2022, which is incorporated herein by reference.

STATEMENT OF FEDERALLY SPONSORED RESEARCH

This invention was made with Government support under contract CA227713 awarded by the National Institutes of Health. The Government has certain rights in the invention.

FIELD OF THE INVENTION

The present invention relates generally to medical imaging. More specifically, it relates to techniques for tomographic image reconstruction.

BACKGROUND OF THE INVENTION

Various tomographic imaging modalities such as X-ray computed tomography (CT), positron emission tomography (PET), magnetic resonance imaging (MRI) are vital tools in modern medicine. The task of volumetric imaging is to create a three-dimensional (3D) representation of an object or body from a set of sensor measurement data, which provides an intermediate representation of the object via spatial encoding of imaging content. A common strategy to transform the sensor data acquired at a lower dimension (e.g., in CT and PET) or a different data domain (e.g., in MRI) to 3D images is through inversion of the encoding function. In unfolding the sensor data to place the right image content to the right voxel, traditional analytical or model-based image reconstruction methods, such as iterative reconstruction based on spatial grid, are used during the reconstruction calculation. Despite their enormous success, these traditional approaches are susceptible to noise, motion artifacts and missing data, thus fail to yield high-fidelity images in sparse sampling scenarios where the Shannon-Nyquist theorem is seriously violated.

Recent advances in deep learning enable data-driven image reconstruction by training deep neural networks to fit the function mapping the input sensor measurements to the target image. Although deep learning has demonstrated impressive performance in image reconstruction and recognition, the model prediction is entirely driven by the training on large-scale dataset. The performance of learning-based model depends on various factors including training data distribution, network structure as well as hyper-parameters, leading to resultant models with little transparency and interpretability. In most existing data-driven techniques, reconstruction of the spatially distributed image content is learned entirely from training data through feature extraction, which may result in geometric misalignment such as in multi-view image processing, especially when the training data are imperfect due to artifacts, noise, or other uncertainties. To accurately reconstruct the 3D images, sophisticated deep neural networks are needed to understand and disentangle the spatial transformation and image content information embedded in the training data, which hinders the acceptance of data-driven approaches in many practical applications.

Current deep learning methods for tomographic image reconstruction are driven entirely by data without consideration of any prior knowledge, which dramatically increases the complexity of neural networks and limits the application scope and generalizability of the resultant models.

In cases of under-sampling scenarios, such as sparse view or ultra-sparse view, there can be severe artifacts in the reconstructed image. To address this issue, image reconstruction algorithms using iterative frameworks have been investigated extensively. In iterative image reconstruction, prior knowledge (i.e., presumed characteristics) is able to be incorporated into the reconstruction process by using a regularization constraint or the maximum a posteriori approach. The prior knowledge can either be the characteristics (e.g., Poisson statistics properties) in the sampling data or the characteristics (piece-wise constant) in the resultant image. Although iterative image reconstruction has the potential to mitigate the image artifacts, especially the artifacts introduced by the low photon statistics, it is still challenging to address aliasing artifacts. Thus, tomographic reconstruction with ultra-sparse sampling remains an open question. This is the reason why modern CT vendors use low tube current instead of sparse view to reduce radiation dose. Meanwhile, it is also a challenge to incorporate complicated prior knowledge into the iterative framework which may result in a nonconvergent objective function.

Substantial effort has been made to accelerate MRI acquisition by reconstructing MRI images from sparsely sampled k-space data, including compressed sensing-based methods and low rank model-based methods, where prior knowledge of imaging subjects, such as sparsity in a transform domain or low rankness of image matrices were exploited to regularize the ill-posed problem of reconstructing MRI from subsampled k-space data. More recently, deep neural networks that are capable of learning complex data-driven priors from a training dataset have shown improved performance over conventional methods that use pre-defined priors. The acceleration factor is, however, still insufficient in supporting volumetric motion tracking during MRI-guided radiotherapy, which requires sub-second temporal resolution to capture patient dynamics. A fundamental deficiency of most deep learning-based methods is that the reconstruction process is purely data-driven. The prior knowledge of k-space sampling pattern is used at most as a consistency constraint for algorithm estimations at sampled k-space locations.

Tomographic image reconstruction with sparse sampled data remains a challenge for both traditional and data-driven reconstruction approaches.

SUMMARY OF THE INVENTION

In one aspect, the invention provides a methodology for deep learning-based image reconstruction by incorporating the physics or geometry priors of the imaging system with deep neural networks, which may be applied to various imaging modalities such as CT and MRI. The approach may be outlined as follows:

1. A deep neural network used to complete the sensor measurements field through data-driven network training. For example, the network can learn to generate novel-view projection data for CT imaging or synthesize unacquired k-space samples for MRI imaging.

2. A physics module based on the imaging system is used to map the sensor measurements field to image space, which bridges the transformation across different spaces based on the physics and geometry priors of the corresponding imaging system.

3. Another deep neural network is used to complete the image space data through data-driven network training and output the final reconstructed image.

In one aspect, the invention provides a method for medical imaging comprising: performing a sparse-sampled tomographic imaging acquisition by an imaging system to produce acquired sparse imaging samples; synthesizing by a first deep learning network unacquired imaging samples from the acquired imaging samples to produce complete imaging samples comprising both the acquired imaging samples and unacquired imaging samples; transforming by a physics module the complete imaging samples to image space data based on physics and geometry priors of the imaging system; and performing image refinement by a second deep learning network tomographic images from the image space data. Preferably, the physics and geometry priors of the imaging system comprise geometric priors of a physical imaging model of the imaging system, and prior geometric relationships between the sample and image data domains.

In one implementation, we focus on volumetric tomographic image reconstruction from 2D projections by establishing a framework of 2D view synthesis and geometry-embedded image reconstruction model. The main insight inferred from this work is that the dual-domain learning should be performed in both 2D projection domain and 3D image domain, with the geometry priors introduced to bridge the dimensionality gap between 2D projection domain and 3D image domain through a deterministic back-projection transformation. In this way, the view synthesis module in the 2D projection domain can help to relieve the burden in image refinement, which is especially beneficial in the ultra-sparse sampling settings.

In one implementation, the imaging system is a CT imaging system. The synthesized unacquired imaging samples may be novel-view projections of the CT imaging system. The physics model may include a geometric back-projection operator to transform 2D projections to 3D images based on known geometric properties of the imaging system.

In another implementation, the imaging system is an MRI imaging system. The synthesized unacquired imaging samples may be k-space samples of the MRI imaging system. The physics module may include a physics-aware image reconstruction framework trained to reconstruct volumetric MRI images from ultra-sparse k-space samples based on both known k-space sampling patterns and fixed transformations between k-space and image space. The physics module preferably transforms k-space samples to volumetric images by using known k-space sampling patterns of the MRI imaging system and fixed transformations of the MRI imaging system between k-space and image space.

BRIEF DESCRIPTION OF THE DRAWINGS

FIG. 5A 3D image refinement network (3D-Net) learns to refine the geometry-preserving 3D images (GPIs) to reconstruct the final 3D image.

FIG. 9A 2D generation network that synthesizes new 2D representations associated with unacquired k-space samples. FIG. 9B Geometry module that utilizes both sampling pattern and known k-space-to-image domain transforms to generate volumetric representations. FIG. 9C 3D refinement network that refines image quality for final volumetric image reconstruction.

DETAILED DESCRIPTION OF THE INVENTION

Figure 1:
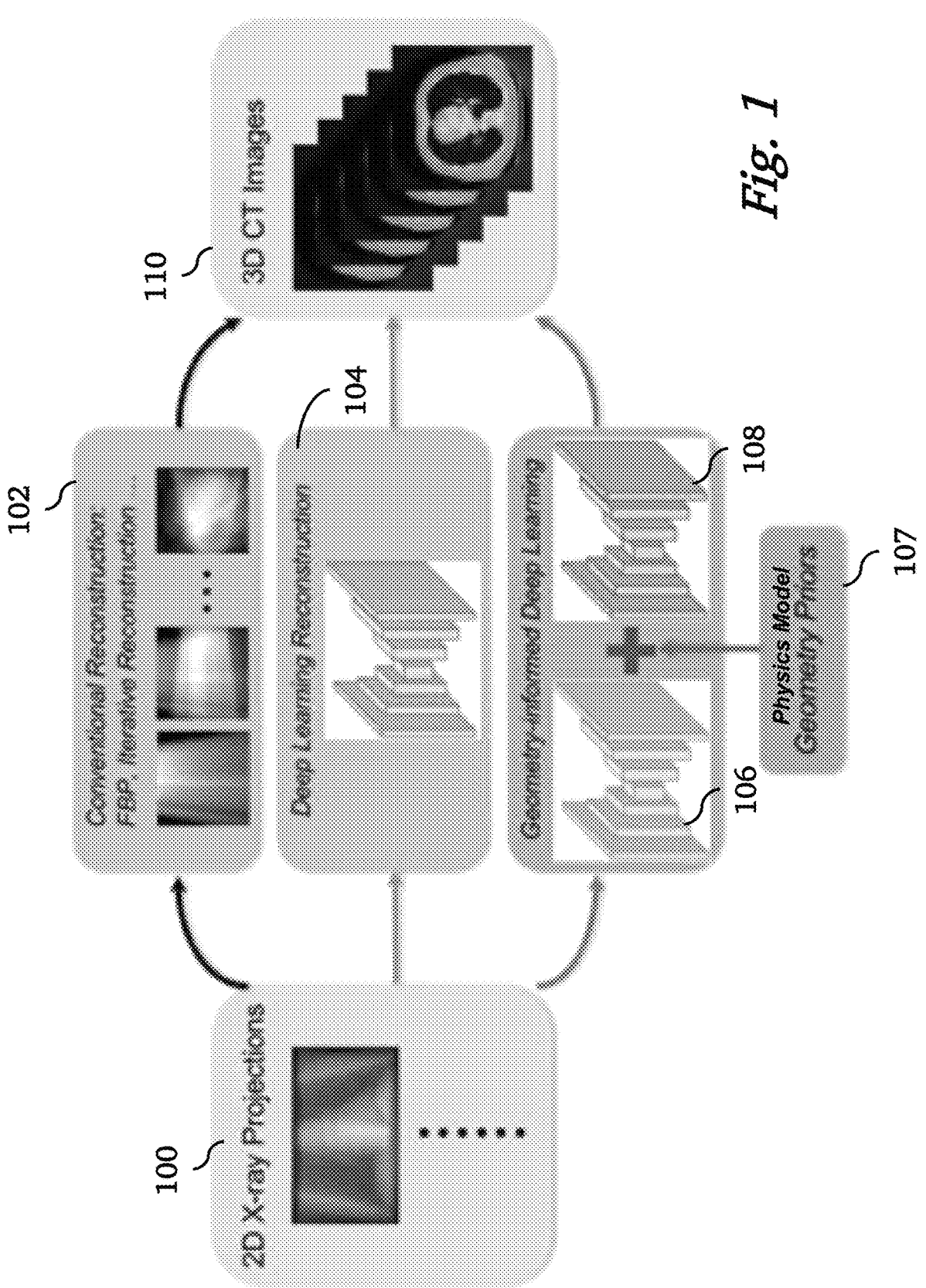
FIG. 1. Different 3D tomographic image reconstruction methods. Among different categories of CT reconstruction algorithms, the geometry-informed deep learning approach not only learns the mapping function driven by large-scale training data, but also integrates geometric priors to bridge the dimensionality gap between the 2D projection domain and 3D image domain.

The invention may be implemented in different imaging modalities such as CT and MRI. In the description below, the principles and methods of the invention will be illustrated using examples from these two imaging modalities. Common to both implementations is the integration of physics and geometry priors into a deep learning approach for tomographic image reconstruction.

CT Implementation

X-ray imaging is a widely used approach to view the internal structure of a subject for clinical diagnosis, image-guided interventions and decision-making. The X-ray projections acquired at different view angles provide complementary information of patients anatomy and are required for stereoscopic or volumetric imaging of the subject. Obtaining multiple-view projections inevitably increases radiation dose and complicates clinical workflow. In an embodiment of the invention implemented for CT image reconstruction, a deep learning-based geometry-integrated projection synthesis framework is provided for synthesizing novel-view X-ray projections. This geometry-informed deep learning framework is able to provide 3D tomographic image reconstruction from ultra-sparse data. This framework integrates geometric priors of the physical imaging model into a deep learning framework.

We describe a strategy for obtaining X-ray image at a novel view angle from a given projection at a specific view angle to alleviate the need for actual projection measurement. Specifically, a deep learning-based geometry-integrated projection synthesis (DL-GIPS) framework is provided for the generation of novel-view X-ray projections. This deep learning model extracts geometry and texture features from a source-view projection, and then conducts geometry transformation on the geometry features to accommodate the view angle change. At the final stage, the X-ray projection in the target view from the transformed geometry and texture features is synthesized via an image generator. The feasibility and potential impact of the DL-GIPS model are demonstrated using lung imaging cases. The strategy can be generalized to a general case of multiple projections synthesis from multiple input views and provides a new paradigm for various stereoscopic and volumetric imaging with substantially reduced efforts in data acquisition.

The approach can also be generalized to a more general synthesis from multi-views to multi-views projections. This deep learning-based geometry-integrated projection synthesis model generates novel-view X-ray projections through feature disentanglement and geometry transformation. The approach is validated using X-ray projections across various lung patients.

Here we describe a geometry-informed deep learning framework for ultra-sparse tomographic image reconstruction. We describe an effective strategy of incorporating prior geometric relationship between the input and output data domains to augment the data-driven tomographic x-ray imaging. This geometry-informed image reconstruction (GIIR) relieves the burden for the model to gain comprehension of the system geometry and allows the model to focus on learning other sematic unknowns. We show that the approach makes high-fidelity data-driven image reconstruction possible, even in the limit of ultra-sparse sampling where the most sophisticated iterative reconstruction with regularization and current data-driven deep learning approaches would fail to yield artifact-free images. Generally, in tomographic CT imaging, the 2D projection x-ray measurements represent the sensor data that encode the internal anatomy of the 3D subject, with the encoding function determined by the physics of the x-ray and media interaction. Specifically, GIIR framework includes three modules: a) a 2D projection generation network (2D-Net) is developed to learn to generate novel-view projections from the given sparse views; b) a geometric back-projection operator transforms the 2D projections to 3D images, referred to as geometric preserving images, which geometrically relates the pixelated 2D input data to the corresponding ray lines in 3D space; and c) a 3D image refinement network (3D-Net) learns to refine the GPIs to generate the final 3D images. We demonstrate that the seamless inclusion of known priors is essential to enhance the performance of volumetric computed tomography imaging with ultra-sparse sampling. The invention opens new avenues for data-driven biomedical imaging and promises to provide substantially improved imaging tools for various clinical imaging and image-guided interventions.

This approach provides tomographic imaging with significantly reduced imaging dose and simplified hardware design with substantially reduced efforts in data acquisition. In addition to diagnostic imaging, it can be used in various clinical applications, such as image-guided radiation therapy and intervention. It may also be used for generation of volumetric images for applications such as treatment planning and dose calculation in clinical cancer treatment, disease diagnosis and decision making.

The approach provides a feasible solution to synthesize novel-view X-ray projections from a specific view X-ray projection, which can also be generalized to synthesizing multiple projections. This geometry-informed deep learning framework for ultra-sparse tomographic image reconstruction provides a mechanism for the integration of geometric priors of the imaging system, which is more robustly generalized across different patients especially with sparse sampling.

This strategy of incorporating the prior geometric relationship between the input and output data domains to augment the data-driven learn-based tomographic x-ray imaging relieves the burden for the model to gain comprehension of the system geometry and allows the model to focus on learning other sematic unknowns. The approach makes high-fidelity data-driven image reconstruction possible, even in the limit of ultra-sparse sampling where the most sophisticated iterative reconstruction with regularization fail to yield artifact-free images. The model outperforms current data-driven deep learning approaches.

FIG. 1 is a schematic overview comparing tomographic image reconstruction approaches. Generally, in tomographic 3D CT imaging, the 2D projection x-ray measurements 100 are the acquired raw sensor data that encode the internal anatomy of the 3D subject, with the encoding function determined by the physics of the x-ray and media interaction. The goal is to reconstruct from the sensor measurements 100 the 3D computed tomography images 110 which are stored and displayed for medical purposes. In conventional reconstruction 102, techniques such as filtered back-propagation (FBP) and iterative reconstruction are used to perform the reconstruction. Alternatively, in conventional data-driven deep learning reconstruction 104, the 2D acquired projection data are fed to a neural network that has been trained to generate directly the tomographic images 110 as output. In contrast with these conventional approaches, the present approach uses two separately trained neural networks 106, 108 with a physics module 107 based on geometry priors between them.

Figure 2:
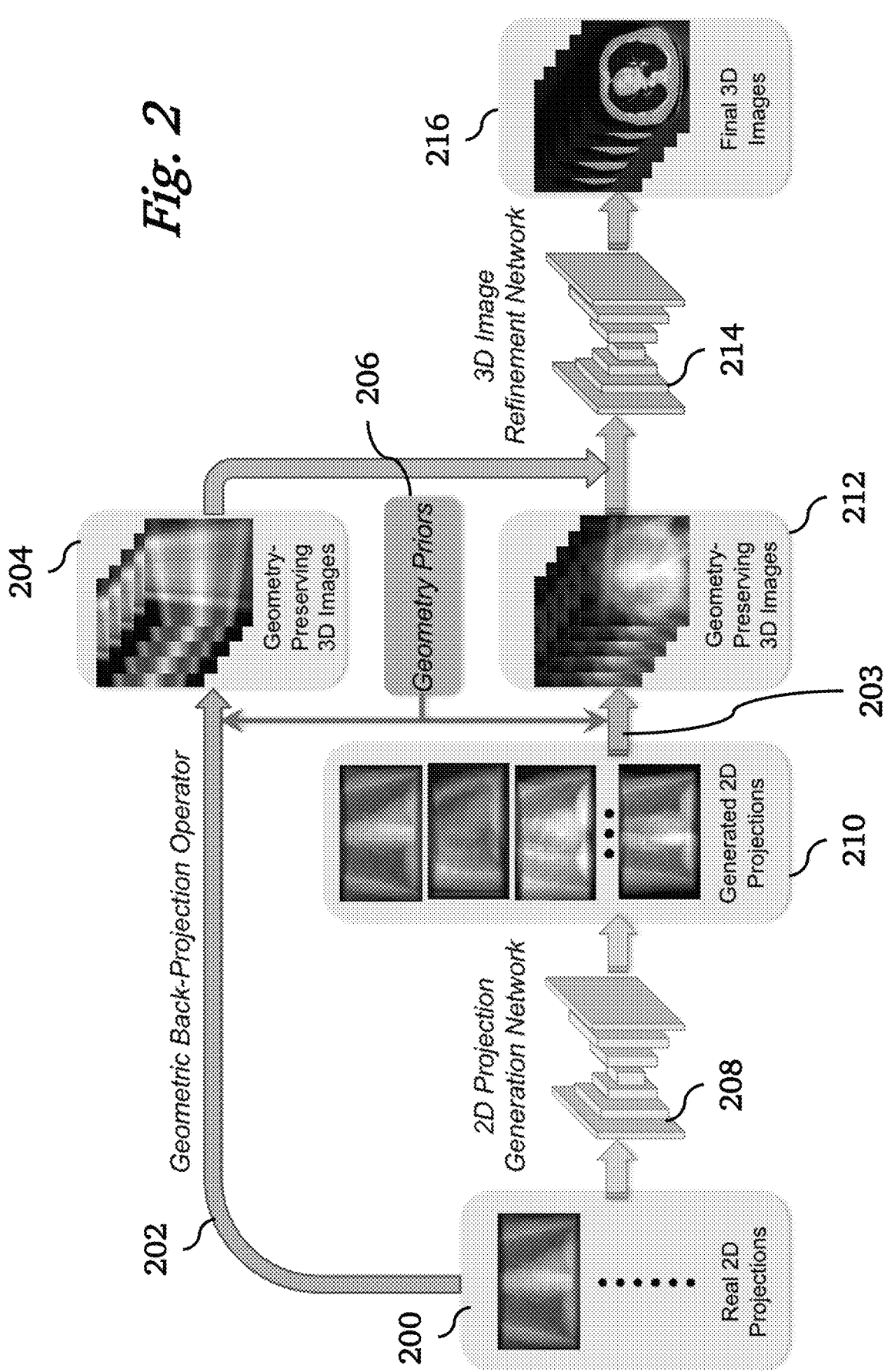
FIG. 2. Geometry-informed image reconstruction (GIIR). Overall framework of GIIR model with dual-domain learning modules of 2D projection generation network (orange arrows), 3D image refinement network (blue arrows) and the back-projection operator (purple arrows) of geometric transformation.

FIG. 2 is a data flow diagram illustrating the overall framework of a GIIR model, according to an embodiment of the invention. Real 2D projection data 200 is transformed to 3D tomographic images 216 using neural networks 208 and 214 with a physics module 202, 203, 206 between them. The physics model integrates the known imaging geometry 206 of the imaging system into the dual-domain deep learning.

A 2D projection generation network (2D-Net) 208 (see also FIG. 3) is trained to generate novel-view projections 210 from the given sparse views 200. The 2D-Net takes the input projections to generate new projections in other view angles.

Using geometry priors 206, a geometric back-projection operator 202, 203 (see also FIG. 4) transforms the 2D projections 200 and 210 to 3D images 204 and 212, respectively, referred as geometric preserving images (GPIs). In other words, the input projections and the newly generated projections are then independently back-projected to the 3D space to yield two sets of GPIs, which relates the 2D pixels in the projections to their corresponding ray lines in 3D space. This back-projection operator 202, 203 geometrically relates the pixelated 2D input data to the corresponding ray-lines in 3D space.

A 3D image refinement network (3D-Net) 214 (see also FIG. 5) is trained to refine the combined GPIs 204 and 212 to reconstruct the final 3D images 216. That is, the 3D-Net takes the two GPIs as input to reconstruct the final 3D volumetric images. In addition to the information from input 2D projections, the GPIs also inform the 3D-Net with the underlying imaging system geometry through unfolding the pixel-wise intensity of the 2D projections back to the corresponding voxels in the 3D image space through ray tracing.

The 2D-Net 208 and 3D-Net 214 are trained to learn how to complete the missing information in 2D projection domain and 3D image domain, respectively. The back-projection operator is a physics module that provides the underlying geometry link between the 2D and 3D image domains without any learned parameter. In this way, the information encoded in the sparse projections is partially unfolded back to the 3D image space deterministically, which greatly simplifies the overall learning task and facilitates the information flow from 2D to 3D image domains. This strategy allows the network to maximally exploit the information buried in the training data. Practically, GIIR pushes the CT imaging to ultra-sparse limit, which provides a viable solution for volumetric imaging with significantly reduced imaging dose and simplified hardware design.

Key features of this approach include:
A geometry-informed deep learning framework for ultra-sparse 3D tomographic image reconstruction (GIIR) by integrating geometric priors of the imaging system to bridge 2D and 3D image space.

2D projection generation network to synthesize novel-view X-ray projections via representation disentanglement, which further contributes to 3D tomographic image reconstruction.

The 2D network module 208, physics module 202, 203, 206, and 3D network 214 will now be described in more detail.

Firstly, we cast the inverse problem of 3D image reconstruction from 2D projection(s) into a data-driven framework. Given a sequence of 2D projections denoted as $\{p_1, p_2, \ldots p_n\}$, where $p_i \in \mathbb{R}^{H_{2D} \times W_{2D}}$ ($1 \leq i \leq n$) and n is the number of given 2D projections, the goal is to generate a volumetric 3D image I representing the internal anatomy of the subject. With the 2D projections as input, the deep learning model outputs the predicted 3D volume denoted as $I_{pred} \in \mathbb{R}^{C_{3D} \times H_{3D} \times W_{3D}}$, where $I_{truth} \in \mathbb{R}^{C_{3D} \times H_{3D} \times W_{3D}}$ is the ground truth 3D image serving as the reconstruction target. Note that network prediction $I_{pred}$ is of the same size as ground truth image $I_{truth}$, where each entry is a voxel-wise intensity. Thus, the problem is formulated as finding a mapping function $\Phi$ that transforms 2D projections to 3D images. To solve this problem, we develop a GIIR framework to learn the mapping function $\Phi$. As aforementioned, GIIR has three modules: 1) 2D-Net $\phi_1$ with the network weights denoted as $W_1$, 2) geometric back-projection operator $A^*$, where A is the forward projection operator, and 3) 3D-Net $\phi_2$ with the network weights denoted as $W_2$. Thus, the 2D-3D reconstruction process can be formulated as:

$$I_{pred} = \Phi(p_1, p_2, \cdots, p_n) = \phi_2\big(A^*\big(\phi_1\big(p_1, p_2, \cdots, p_n; W_1\big)\big); W_2\big). \quad (1)$$

In the following, we introduce the implementation details of the three modules $\phi_1$, $A^*$, $\phi_2$ in order.

2D Projection Generation Network (2D-Net)

We develop a multi-view X-ray projection synthesis model to generate 2D projections at novel-view angles from sparse input views. Suppose there are m view angles: $X_1, X_2, \ldots, X_m$, and $p_i$ is a projection corresponding to angle $X_i$. $\{p_1, p_2, \ldots, p_m\}$ is a set of paired multi-view projections that depict the underlying imaging subject from different view angles. For each sample, we assume n projections are given as input source views. The goal here is to generate the other (m−n) projections at target view angles and complete missing information in the 2D projection space through deep learning.

To proceed, we assume that the multi-view projections share some latent representations of the underlying imaging subject such as the anatomy structural information, which is named as "content code". Meanwhile, projections at different view angles also contain the view-dependent attributes, named as "attribute code", which is corresponding to the rotation-related characteristics in projections at different view angles. In this way, the novel-view projections could be generated by combining the content code and attribute code. Based on this assumption, we built a 2D projection generation network for multi-view X-ray projections synthesis.

Figure 3:
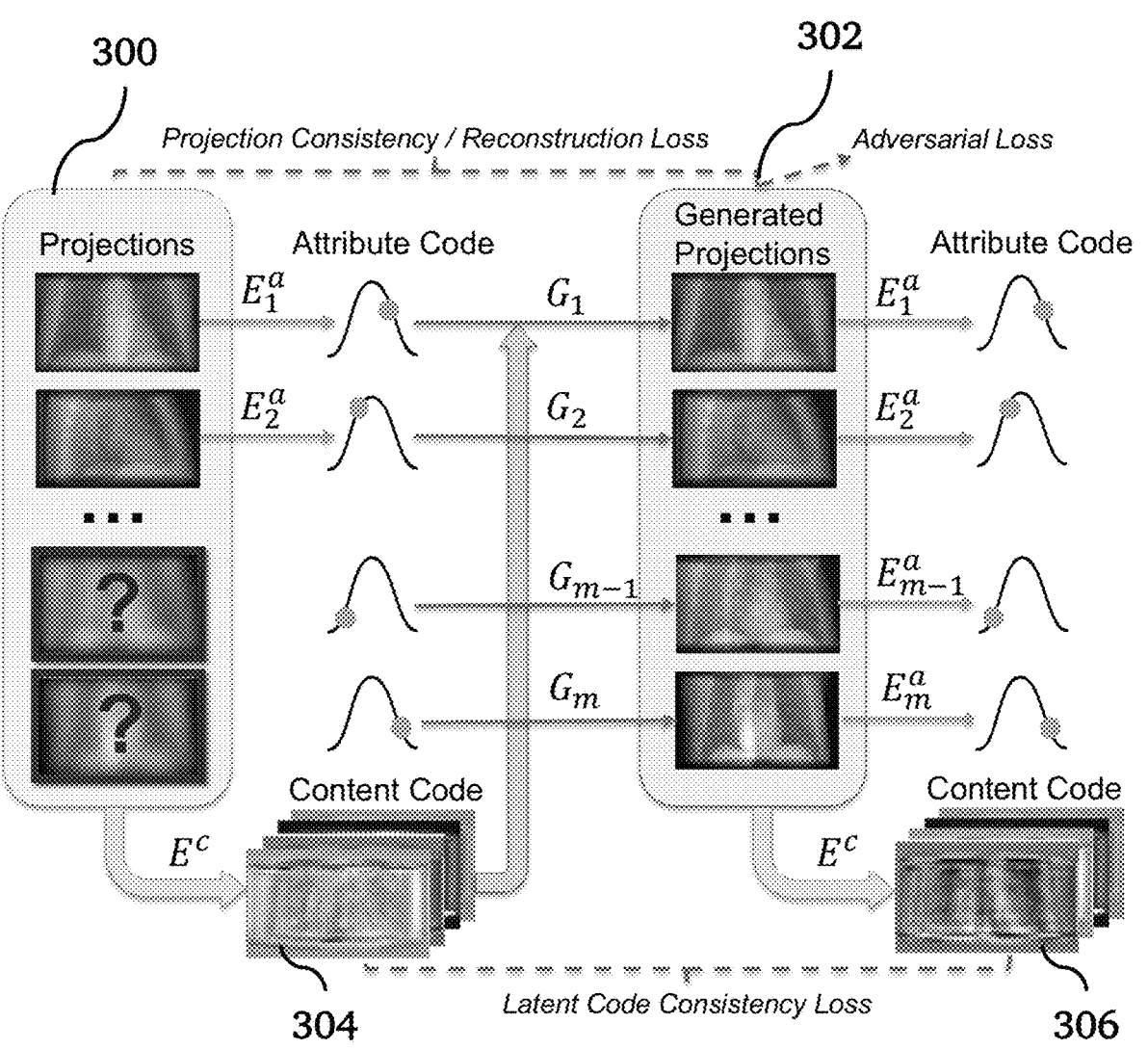
FIG. 3. 2D projection generation network (2D-Net) learns to generate novel views given sparse views (for illustration, two projections are given while unknown views are marked with a red box in inputs). Details of latent codes and loss functions are described in Section III.B.

Specifically, as shown in FIG. 3, the 2D-Net mainly consists of three sub-modules: 1) Across-view content encoder $E^c$: encodes anatomic structural information shared by projections 300, 302 from different view angles to generate content codes 304, 306 $E^c(p_1, p_2, \ldots, p_m)=c$; 2) View-dependent attribute encoder $E_i^a (1 \le i \le m)$:

encodes information in projections 300, 302 which is exclusively corresponding to different view angles $$E_i^a(p_i) = a_i;$$

and 3) Projection generator $G_i(1 \le i \le m)$: generates novel-view projections 302 by combining across-view and view-dependent information learned from encoders $$G_i(c, a_i) = \hat{p}_t.$$

The model learns to extract and disentangle across-view anatomy information and view-dependent rotation attributes from projections at different view angles through a data-driven deep learning approach. Note that the content encoder takes the input with m views. For the input projections where only n source views are known, the other (m−n) views are padded with zeros in the corresponding input channels to ensure consistent input size. We assume the prior distribution for attribute latent code is standard Gaussian distribution $\mathcal{N}$ (0, I) to capture distribution of rotation characteristics. During training, attribute codes of target views are sampled from the prior distribution. For inference, attribute code is fixed and combined with anatomic content to generate target-view projections.

Specifically, the training objectives contain cycle-consistency loss, adversarial loss and reconstruction loss on the generated projections. Firstly, for input source-view projections, the generated projections after the encoding and decoding should recover the original projections. Thus, projection consistency loss adds such a constrain in the cycle of "Projection→Code→Projection".

$$\mathcal{L}_{cyc}^{p_i} = \mathbb{E}_{p_i \sim \mathcal{P}(p_i)}[\| G_i(E^c(p_1, \dots, p_m), E_i^a(p_i)) - p_i \|_1] \quad (2)$$

where $\mathcal{P}$ ($p_i$) is the projection distribution. Likely, the latent codes should also keep consistent in the cycle of "Code→Projection→Code". Thus, the latent code consistency loss can be formulated as follows:

$$\mathcal{L}_{cyc}^{c} = \mathbb{E}_{c \sim \mathcal{P}(c), a_i \sim \mathcal{P}(a_i)}[\| E^c(G_1(c, a_1), \dots G_m(c, a_m)) - c \|_1] \quad (3)$$

$$\mathcal{L}_{cyc}^{a_i} = \mathbb{E}_{c \sim \mathcal{P}(c), a_i \sim \mathcal{P}(a_i)}[\| E_i^a(G_i(c, a_i)) - a_i \|_1] \quad$$

where $\mathcal{P}$ ($a_i$) is the assumed prior distribution of attribute code, which captures various view-dependent characteristics related to different view angles. The content code is sampled from $\mathcal{P}$ (c) by firstly sampling projection distributions $p_i \sim$ $\mathcal{P}$ ($p_i$) $(1 \le i \le m)$ and then getting through content encoder:

$$c = E^c(p_1, p_2, \dots, p_m).$$

To be specific, distribution $\mathcal{P}$ (c) describes various anatomy structures across different patients.

In order to enforce the generated target-view projections to resemble the ground truth projections, we add reconstruction loss for different views as follows in the training objective.

$$\mathcal{L}_{rec}^{p_i} = \mathbb{E}_{c \sim \mathcal{P}(c), a_i \sim \mathcal{P}(a_i)}[\| G_i(c, a_i) - p_i \|_1] \quad (4)$$

Moreover, in recent researches on image generation and reconstruction, adversarial training has shown advantages in providing improved image quality. Therefore, in training the projection synthesis model, we use both reconstruction loss and adversarial loss to improve the image quality of the generated projections. The adversarial loss is defined as follows, with the discriminator $D_i$ to classify between the generated projections and real projections.

$$\mathcal{L}_{adv}^{p_i} = \mathbb{E}_{c \sim \mathcal{P}(c), a_i \sim \mathcal{P}(a_i)}[\log(1 - D_i(G_i(c, a_i)))] + \mathbb{E}_{p_i \sim \mathcal{P}(p_i)}[\log(D_i(p_i))] \quad (5)$$

To sum up, the total training objective is shown as follows, with n projections are given as input source views to generate (m−n) target-view projections.

$$\min_{E^c, E_i^a, G_i} \max_{D_i} \mathcal{L}(E^c, E_1^a, \cdots, E_m^a, G_1, G_m, D_1, \cdots, D_m) = \quad (6)$$

$$\lambda_{cyc}\left(\sum_{i=1}^{n} \mathcal{L}_{cyc}^{p_i} + \sum_{i=1}^{m} \mathcal{L}_{cyc}^{a_i} + \mathcal{L}_{cyc}^{c}\right) + \sum_{i=1}^{m} \left(\lambda_{rec}\mathcal{L}_{rec}^{p_i} + \lambda_{adv}\mathcal{L}_{adv}^{p_i}\right)$$

where $\lambda_{cyc}$, $\lambda_{rec}$, $\lambda_{adv}$ are hyper-parameters of the loss weights. In experiments, we set $\lambda_{cyc}=1$, $\lambda_{rec}=20$, $\lambda_{adv}=1$.

Geometric Back-Projection Operator

Figure 4:
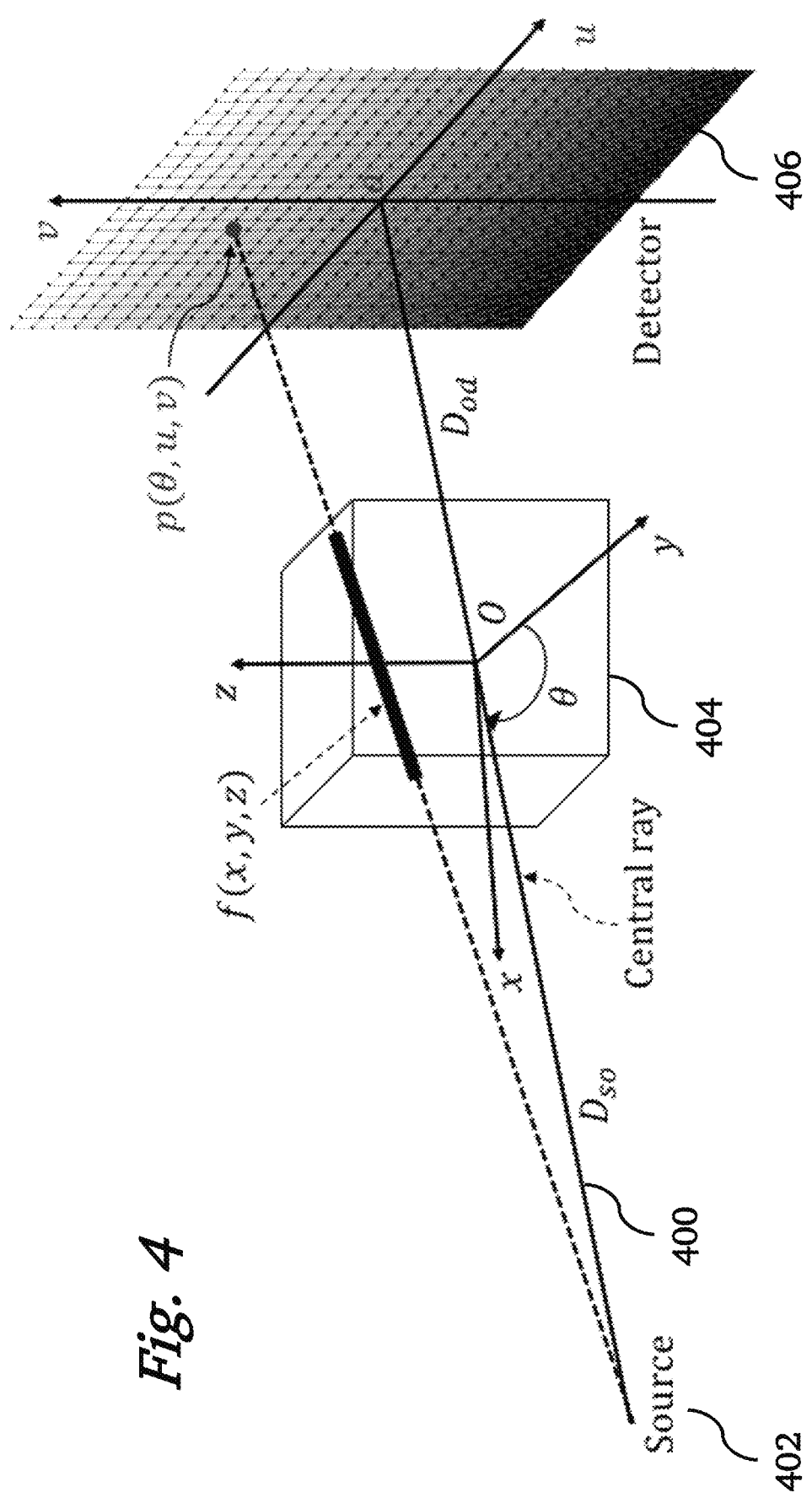
FIG. 4. Geometric back-projection operator unfolds 2D projections to 3D space geometrically to generate geometry-preserving 3D images.

As shown in the perspective schematic diagram of FIG. 4, during X-ray imaging data acquisition, penetrating waves 400 from the source 402 pass through the imaging subject 404 and project onto the detector plane 406 by integrating the intersected voxel intensities in the 3D volume. In this way, multiple X-rays provide projection images of the internal anatomic structure of the imaging subject. In the forward-projection, the geometric relationship between the ray lines of incident X-ray beams and the subject content is determined by the geometry of the imaging system, including the distance between source and volume center of the subject, the distance between volume center and detector plane, the physical size of subject voxels and detector pixels, and the cone-beam geometry and the projection view angles. All this information is relevant geometry priors available from the physical imaging system.

For image reconstruction, we aim to solve the inverse problem to reconstruct the 3D subject volume from 2D projections at different view angles. To relate the 2D projection domain and 3D image domain, we conduct back-projection operation to convert the 2D projections back to the 3D space according to the imaging system geometry as aforementioned. The back-projection operation is based on the same set of geometric relationship as the forward-projection. Specifically, the intensity of a pixel on the 2D projection is placed back to the corresponding voxels of the 3D imaging subject located along the path of the ray line that links the pixel and X-ray source. In this way, the relationship between the pixel-wise intensities on 2D projections and voxel intensities in 3D volumes are incorporated into the 3D image reconstruction.

Therefore, we integrate the imaging geometry into deep learning framework by using the back-projection operation $\mathcal{B}$ to put the pixel intensity back to the corresponding projection line through the point of voxel grid to be reconstructed. The GPI is constructed by aggregating all the projection lines from different view angles. Suppose that the GPI volume to be reconstructed is denoted as $I_{GPI}(x, y, z)$ with x, y, z representing a point in 3D image space based on the 3D coordinate system. Mathematically, the back-projection operation $\mathcal{B}$ can be formulated by the following equation:

$$I_{GPI}(x,y,z)=\mathcal{B}\{p\}=\Sigma_{\theta\in\Omega}p(\theta,u(x,y,\theta),v(x,y,z,\theta))\qquad(7)$$

where p is the assemble of input projections $\{p_1, p_2, \ldots, p_n\}$, $\theta$ is the view angle of a specific projection, $\Omega$ is the assemble of all view angles of input projections, u and v are the ray-projected positions in the detector coordinate system, which can be calculated as follows:

$$u(x, y, \theta) = \frac{x\cos\theta + y\sin\theta}{D_{so} + x\sin\theta - y\cos\theta}D_{sd}\qquad(8)$$

$$v(x, y, z, \theta) = \frac{D_{sd}}{D_{so} + x\sin\theta - y\cos\theta}z\qquad(9)$$

Here $D_{so}$ is the source-to-isocenter distance and $D_{sd}$ is the source-to-detector distance. In this study, we use the geometry of Varian TrueBeam onboard imager with $D_{so}$=1000 mm, and $D_{sd}$=1500 mm. The 3D back-projection operation was implemented using GPU-based parallel computing with CUDA C programming language. Using back-projection operation, both input sparse-view projections and generated novel-view projections are projected back to 3D image space based on the ray traces, in which the geometry of tomography imaging is integrated to bridge 2D-3D image domains. Note that geometric back-projection is a deterministic transformation, which does not need to learn any parameter.

3D Image Refinement Network (3D-Net)

By using the geometric back-projection operator, the two GPIs are produced from the input source-view projections $$I_{GPI}^{src} = A^*(p_1, p_2, \ldots, p_n),$$

and the newly generated novel-view projections $$I_{GPI}^{gen} = A^*(\phi_1(p_1, p_2, \ldots, p_n; W_1).$$

Figure 5A:
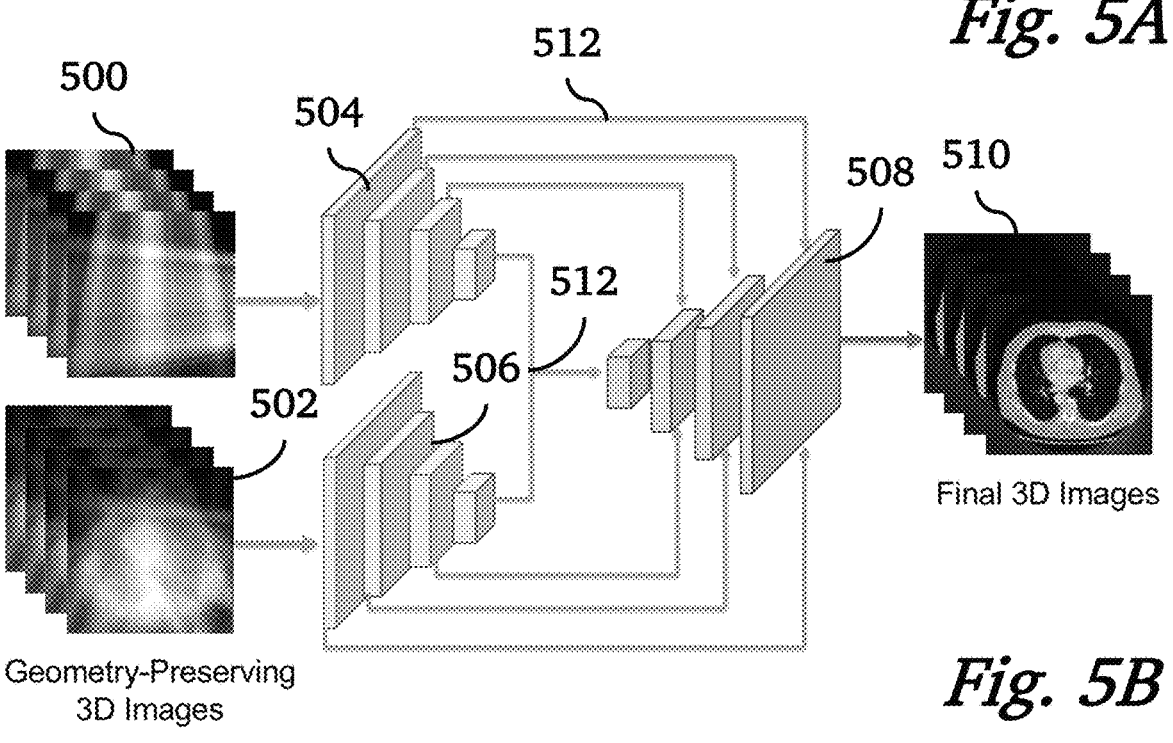
Figure 5B:
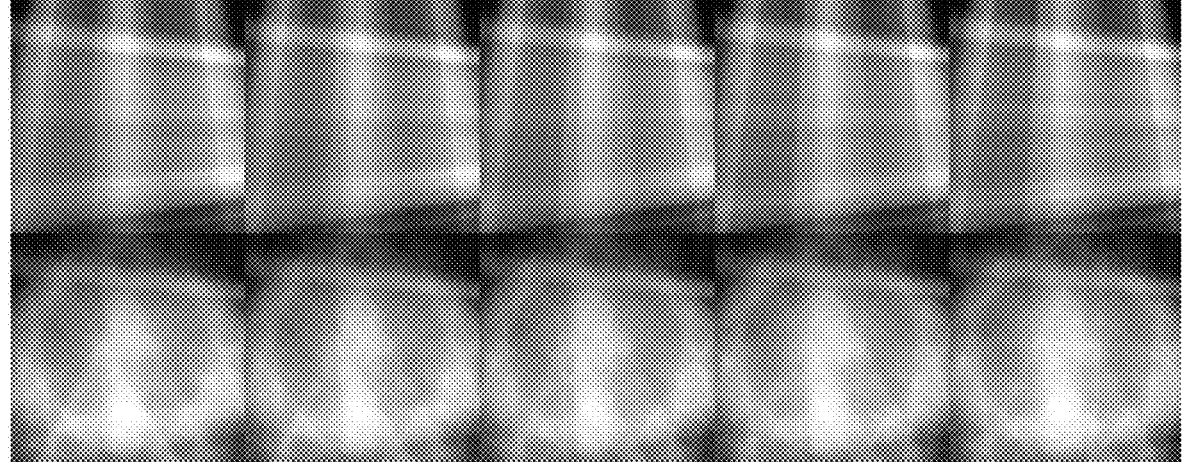
FIG. 5B Example of cross-sectional slices of GPIs with 2 input source views, as the input to 3D-Net. Top row is the GPI produced from the input source-view projections. Bottom row is the GPI produced from generated novel-view projections.

As shown in FIG. 5A, two GPIs 500, 502 are input to two encoder branches 504, 506 of the 3D-Net. These are combined with a decoder branch 508 that generates the final output tomographic images 510. The 3D-Net is trained to complete information in image domain and generate final 3D images:

$$I_{pred} = \phi_2(I_{GPI}^{src}, I_{GPI}^{gen}; W_2).$$

The network architecture is built up on top of a backbone 3D U-Net structure with an encoder-decoder framework 504, 506, 508 and skip connections 512. In our model, the features of two input GPIs are extracted by using two parallel encoder branches 504, 506. For this purpose, a variant Y-shape model is constructed to learn the image refinement with a specific example of GPIs as input to 3D-Net shown in FIG. 5B. Specifically, the Y-shape network is constructed to incorporate the information from both the given source-view projections and the generated novel-view projections. The given input projections are very sparse but all the pixel-wise intensities in the source-view projections are accurate and reliable. Therefore, these data are able to regularize the generated novel-view projections, which may have uncertainty in intensity distribution due to their synthetic nature. It is worthwhile to note that these generated projections could provide a geometry-preserving image with more outstanding anatomic object structures, which simplifies the subsequent learning of image refinement network. Thus, a Y-shape network structure is constructed for 3D image refinement to reconstruct final 3D image.

To be specific, the encoder 504, 506 has four down-sampling blocks to learn hierarchical representations from the input GPIs 500, 502. Each down-sampling block contains two 3D convolution layers with a kernel size of three. Each convolution layer is followed by a rectified linear unit activation (ReLU) layer and a group normalization layer. Each down-sampling block doubles the channel of feature maps with initial number of feature maps as 32 in the first block. The down-sampling is implemented by a max pooling layer with a step size of (2, 2, 2). Asymmetrically, the decoder 508 has four up-sampling blocks to generate final 3D images 510 from the representations learned from the encoder. Each up-sampling block contains two 3D convolution layers with a kernel size of three, followed by a ReLU layer and a group normalization layer. We use interpolation function to conduct up-sampling operations. In order to establish the hierarchical skip connections between two encoders 504, 506 and the one decoder 508, we concatenate 512 the feature maps from both encoders and connect to the corresponding feature level in the decoder. In this way, we force the model to utilize information from both the input sparse-view projections and the generated novel-view projections to reconstruct final 3D images. Finally, we use another 3D convolution layer with kernel size of one and tangent activation to output the final 3D image with the expected size and data range. The loss function to optimize 3D image refinement network is:

$$\min_{W_2} \mathcal{L}(W_2) = \mathbb{E}\left[\left\|\phi_2(I_{GPI}^{src}, I_{GPI}^{gen}; W_2) - I_{truth}\right\|_1\right]\qquad(10)$$

We now discuss experiments to validate the approach.

Dataset

To evaluate the approach, we conduct experiments on a public dataset: The Lung Image Database Consortium and Image Database Resource Initiative (LIDC-IDRI). The dataset contains 1018 patient cases, each including a volumetric image from a clinical thoracic CT scan. Here, we regard each case as an independent data sample.

In data pre-processing, we resample all the CT images to the same 1 mm resolution in z-axis direction and resize cross-sectional images on the xy-plane to the size of 128×128. In experiments, 80% of the data (815 samples) are used for training and validation, while 20% of the data (203 samples) are held out for testing. For each 3D CT image, the 2D projections or digitally reconstructed radiographs (DRRs) in different view angles are obtained by projecting the 3D CT image along respective directions, with the geometry defined by a clinical on-board cone-beam CT imager of TrueBeam system (Varian Medical System, Palo Alto, CA) for radiation therapy. During training, following the standard protocol of data pre-processing, we conduct scaling normalization for both 2D projections and 3D images, where pixel-wise or voxel-wise intensities are normalized to the data range [−1, 1].

Training

With the given 2D projections $\{p_1, p_2, \ldots, p_n\}$ the GIIR model aims at predicting the 3D image $I_{pred}$ as close as possible to the ground-truth 3D image $I_{truth}$ The two deep networks are implemented using PyTorch and trained separately by using Adam optimizer. In the training of 2D-Net, we use mini-batch size of 1 and initial learning rate of 0.0001, which is decayed by 0.5 for every 100000 iterations with a total of 110000 iterations. For the training of 3D-Net, mini-batch size is 3 and initial learning rate is 0.0002, which is decayed by 0.2 for every 20000 iterations with a total of 30000 iterations. The baseline model adopts the same training strategy as the 3D-Net. The validation set, which is randomly selected from the training set, is used to tune the hyper-parameters. After finalizing the model structure and hyper-parameters, we use all the training data (815 samples) to train the model and evaluate on the held-out testing set (203 samples). We trained the network using one Nvidia Tesla V100 GPU.

Testing

Various quantitative metrics are employed to measure the reconstructed 3D images: normalized root mean-squared error (NRMSE), structural similarity (SSIM), and peak signal-to-noise-ratio (PSNR). In general, a lower value of NRMSE or a higher SSIM score indicates a better reconstructed image that is closer to the ground-truth. Higher PSNR is always desirable as it implies a better image quality. The same metrics are also used to evaluate the intermediate results of 2D-Net and 3D-Net.

Results

To evaluate the proposed approach, we conduct experiments on a dataset of 1018 lung CT images of different patients. The 2D-Net is trained by the projection data from different view angles, while the 3D-Net is trained with the paired data of GPIs and ground-truth 3D images. In our study, the anterior-posterior (AP) projection (0-degree) is used as input for single-view reconstruction. The AP and lateral (90-degree) projections are for two-view reconstruction. When more projections are sampled (n≥3), they are distributed evenly over the 360 degrees. The target 3D images are the fully sampled CT images reconstructed from 720 projections as used in standard clinical protocol. Following, we demonstrate the results of ultra-sparse view CT reconstruction, as well as intermediate results.

2D Projection Generation

Figure 6:
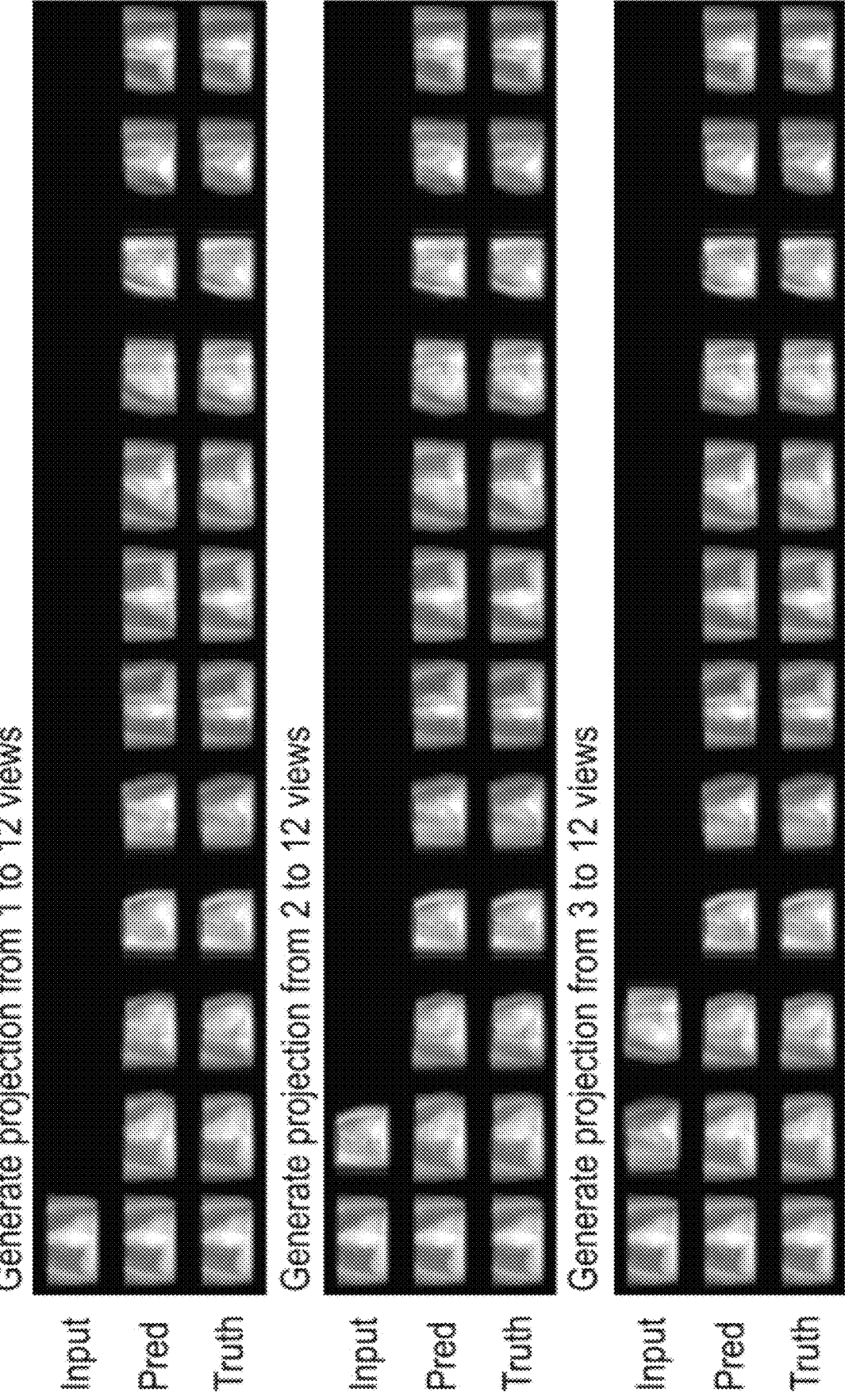
FIG. 6. Results of 2D-Net for generating novel-view projections. Predicted and ground-truth 2D projections (12 angular views evenly distributed over 360 degrees) of a testing sample (with 1-3 input projections respectively). For each group of results, the input projections fed into the network, the predicted novel-view projections output from the network, and the ground-truth of novel-view projections are shown row by row.

We first evaluate the 2D-Net performance in generating novel-view projections. Experimentally, the network (FIG. 3) is trained to generate 12 projections from 1-3 input projection(s). The choice of the number of generated projections is set in terms of the trade-off between obtaining informative GPIs capturing sufficient object information and avoiding too much error accumulation from projection synthesis. We deploy the trained network on held-out testing dataset. FIG. 6 shows generated projections of a testing sample.

It is remarkable that 2D-Net could generate novel-view projections that resemble the targets with high fidelity, even given only ultra-sparse input projections. The model generalizes well across different subjects with various anatomy structures. Increasing input views can provide more structural information, resulting in more accurate synthesized projections in novel-view angles.

Simplified GIIR for 3D Reconstruction

In order to comprehend the significant role of geometric priors and the functionality of 3D-Net, we first construct a simplified GIIR reconstruction model containing only back-projection operation and 3D-Net without 2D-Net. Specifically, we apply geometric back-projection operator to the input 2D projections to produce the GPIs, which then get through the 3D-Net for reconstructing 3D images. Note that, here, all the inputs are ground-truth 2D projections, and the 3D-Net is trained by using the corresponding GPI from only the ground-truth 2D projections.

Figure 7:
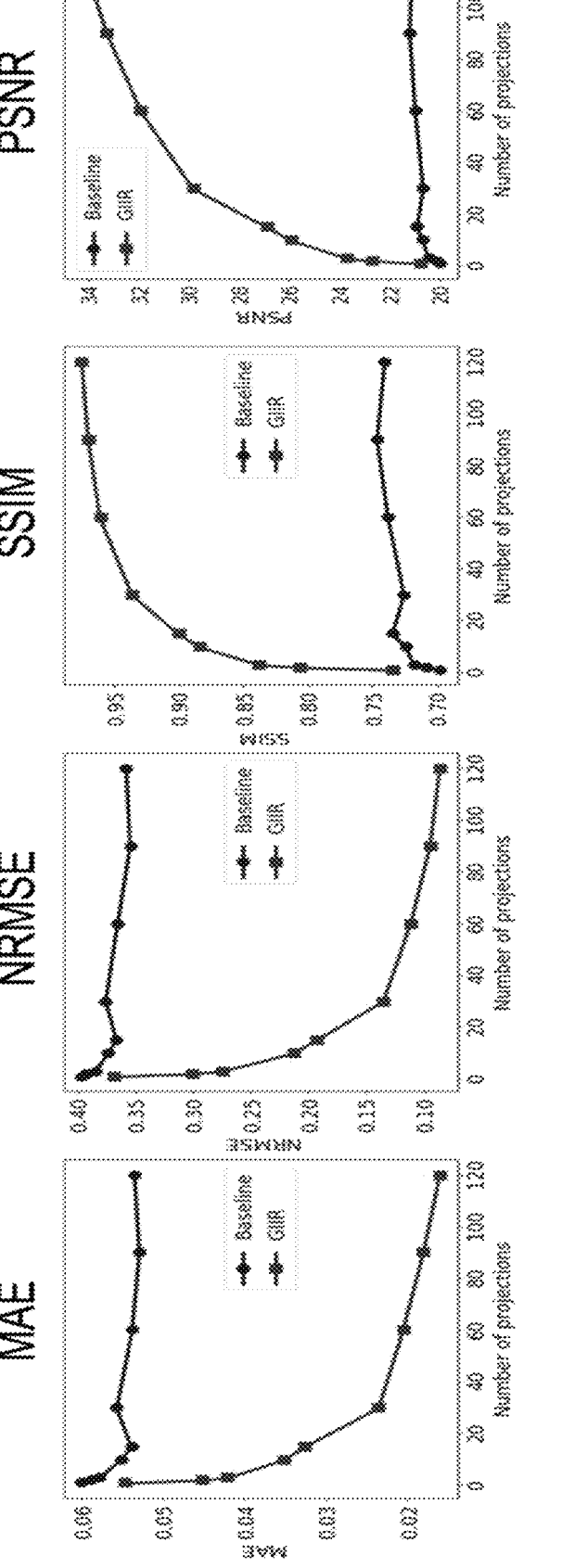
FIG. 7. Evaluation results of "Baseline" model (without inclusion of geometry) sand "GIIR" model (with geometry) for different numbers of input projections. The x axis indicates the number of projections given as inputs. The y axis shows the values of evaluation metrics, MAE, NRMSE, SSIM, and PSNR. For reference, MAE, NRMSE, SSIM for fully sampled ground truth images are 0, 0, 1 respectively, while PSNR is not defined.

We conduct experiments using different number of projections (10~120) as input views. With the increasing input projections, the whole model is trained separately regarding to the specific input projection pattern. During testing, the trained model is deployed under the same setting as training. We plot the averaged evaluation metrics (MAE, NRMSE, SSIM, PSNR) against the number of input projections as the curve in FIG. 7 denoted as "GIIR" when input projections are more than 10. These results show that, as compared with baseline model results obtained without geometric priors, incorporation of prior geometric information leads to better reconstructed 3D images. This trend continues as the number of projections increases, but the improvement saturates as more and more projections are provided. The "knee" point in the curve appears around 30 projections.

Note that we conduct experiments with more views beyond the ultra-sparse limit, in order to study the "knee" point and plateau in the performance curve. Here, we compared the simplified GIIR model with only the baseline model in different numbers of views to demonstrate the consistent advantage of adding geometry priors with the presence of more projections. In reality, as the number of input projections increases, more algorithms become available to solve the sparse tomographic reconstruction problem. In our study, with simplified GIIR, the incorporation of geometric priors could greatly compensate the missing information caused by sparse sampling and yield CT images closer to the fully sampled CT (reconstructed from 720 projections), especially when the angular sampling is over 30 projections. But when it comes to more sparse sampling, we observe that the image quality deteriorates gradually as projection number decreases, from FIG. 7. Thus, ultra-sparse view reconstruction needs to be tackled more carefully.

GIIR for Ultra-Sparse 3D Reconstruction

Based on above studies, in order to reconstruct volumetric images with ultra-sparse sampling, either more sophisticated network architecture or additional prior knowledge must be in place. A dual-domain learning framework with incorporation of known geometry priors (FIG. 2) is designed to improve the situation and provide a viable solution for image reconstruction with ultra-sparse sampling. In the proposed GIIR model, two GPIs obtained by back-projecting the ground-truth projections and the generated projections from 2D-Net, are used as inputs to train the two-branch Y-shape 3D-Net simultaneously.

Figure 8A:
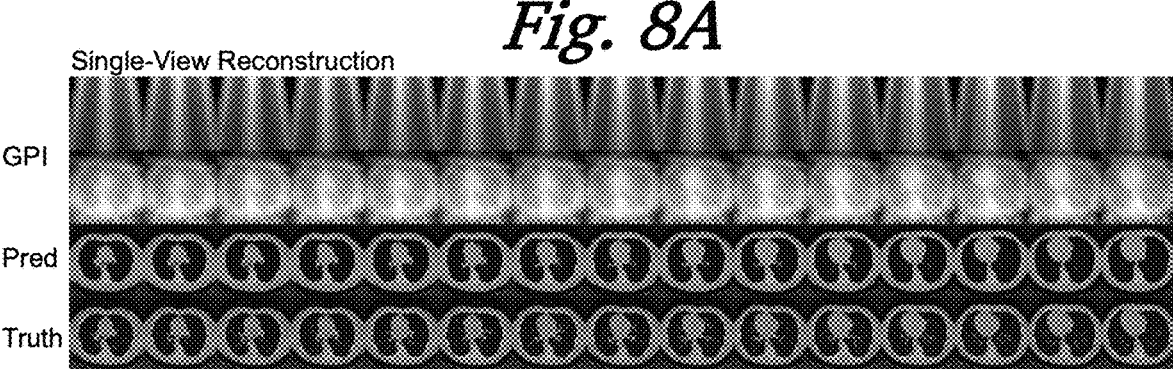
FIGS. 8A-8C. Results of ultra-sparse reconstruction by GIIR model. Here, we show the cross-sectional slices of 3D CT images of the same testing sample from (FIG. 8A) single-view reconstruction, (FIG. 8B) two-view reconstruction, (FIG. 8C) three-view reconstruction, respectively. In each row, cross-sectional slices of ground-truth 3D images, predicted final 3D images, and GPIs, are shown when 1-3 projections are inputted to GIIR model. Two GPIs back-projected from ground-truth projections and generated projections separately serve as inputs to 3D image refinement network.
Figure 8B:
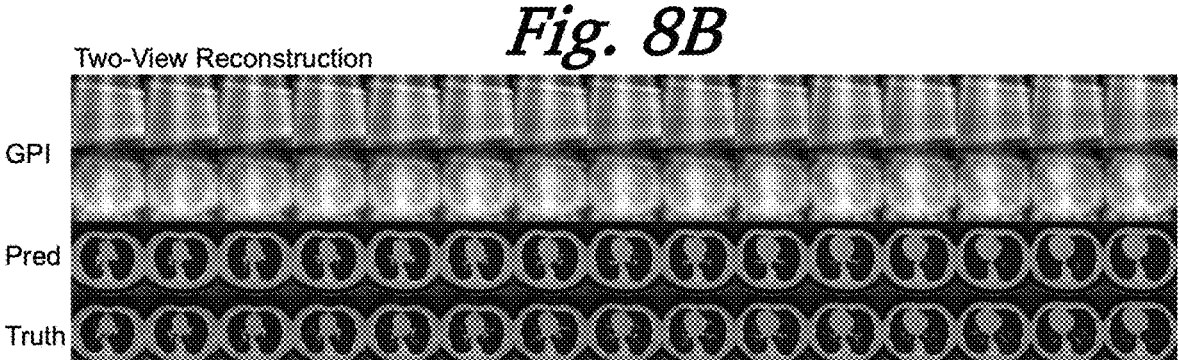
Figure 8C:
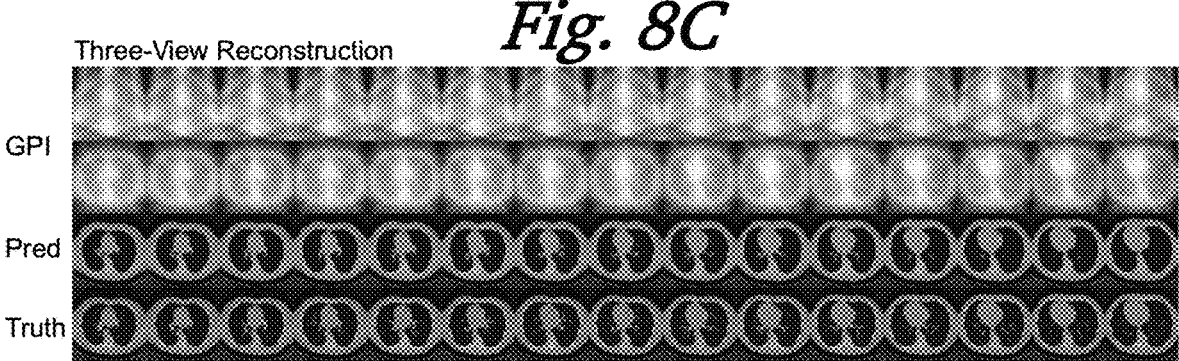

The final results of single-/two-/three-view reconstruction are demonstrated in FIGS. 8A-8C. The corresponding quantitative evaluations averaged across all testing samples are reported in Table 1 denoted as "GIIR", which are also plotted in red curve in FIG. 7 when input projections are 1, 2, 3. It is worth noting that even with ultra-sparse projections, the GIIR model is able to reconstruct 3D CT images with important anatomic structures such as shape, size and boundary of the organs, as shown in FIGS. 8A-8C.

TABLE 1

| Results of Ultra-Sparse-View Reconstruction | | | | | | | | |
| --- | --- | --- | --- | --- | --- | --- | --- | --- |
| Reconstruction | Single-view | | | Two-view | | | Three-view | | |
| Methods | NRMSE ↓ | SSIM ↑ | PSNR ↑ | NRMSE ↓ | SSIM ↑ | PSNR ↑ | NRMSE ↓ | SSIM ↑ | PSNR ↑ |
| Baseline | 0.3961 | 0.6978 | 19.9819 | 0.3927 | 0.7078 | 20.1455 | 0.3841 | 0.7175 | 20.4150 |
| X2CT | 0.3977 | 0.7002 | 20.2308 | 0.3751 | 0.7311 | 20.9120 | — | — | — |
| X2CT (w/ proj. loss) | 0.3766 | 0.7117 | 20.5705 | 0.3596 | 0.7286 | 20.9924 | — | — | — |
| GIIR (w/o two-branch encoder) | 0.4045 | 0.7005 | 19.9672 | 0.3488 | 0.7650 | 21.3140 | 0.2969 | 0.8170 | 23.1444 |
| GIIR | 0.3684 | 0.7341 | 20.7699 | 0.3000 | 0.8067 | 22.6868 | 0.2740 | 0.8378 | 23.6688 |

NRMSE, normalized root mean squared error; SSIM, structural similarity; PSNR, peak signal noise ratio.

Compared Methods

We compare the present method with Baseline model and X2CT model, which are end-to-end data-driven models without any geometric priors. Compared with Baseline and X2CT models, the resultant images from GIIR model provide more reliable structures. To be specific, GIIR reconstructs shapes with more clarity and sharper boundary for liver and cardio organs, which are closer to ground truth compared with baseline and X2CT results. Finally, after averaging across all the testing samples, evaluation metrics reported in Table 1 give a quantitative comparison between different methods. For a fair comparison, we experiment X2CT model with (1) only reconstruction loss (denoted as "X2CT"), and with (2) both reconstruction and projection losses (denoted as "X2CT (w/proj.loss)"). Note that Baseline and GIIR models are trained with only reconstruction loss. To sum up, based on the quantitative and qualitative results comparison, the GIIR method outperforms the baseline and X2CT models in ultra-sparse tomographic image reconstruction.

Moreover, ablative study is conducted to show the importance of using the two-branch encoder in the 3D image refinement network to the final performance of reconstruction. By using a single-branch encoder, only the generated projections are taken as the input to the 3D-Net to reconstruct the final 3D image. The quantitative results of ultra-sparse-view reconstruction are shown in Table 1, denoted as "GIIR (w/o two-branch encoder)". From the results, we see that using two-branch 3D-Net improves the performance. The given input source-view projections are very sparse but all the pixel-wise intensities in the source-view projections are assumed to be accurate and reliable. Therefore, these data are able to regularize the generated novel-view projections, which may have uncertainty in intensity distribution due to their synthetic nature.

Method Comparison

Comparison with the Baseline model helps to investigate the effectiveness of integrating geometry priors. Quantitative evaluations of the Baseline model with regard to different numbers of input projections are plotted in FIG. 7. From the curve, when input projections are more than 30, only small improvement is observed from increasing input views. Intuitively, a model with more input views should perform better. However, how does a data-driven deep network reasons and realizes this common wisdom, is not clear. In order to map input multi-view 2D projections to output 3D image, the deep network needs to apprehend the cross-dimensionality transformation to transfer the knowledge from 2D projection to 3D image domain. In reality, learning such a cross-dimensionality transformation is a highly nontrivial task, especially for a purely data-driven approach. For example, it is challenging for the data-driven algorithm to fuse the extracted semantic features from different input views together without any prior guidance. Even with the multi-branch model, direct learning the multi-view feature fusion and 2D-3D feature transformation with a large number of input projections through a data-driven approach is not an easy task. However, the proposed strategy allows us to combine the knowledge from multiple views with reduced ambiguity and enhance the ultimate success of 3D image reconstruction. To sum up, the GIIR model with geometry priors outperforms the baseline model without geometry priors. With more than one input projections, the improvement of GIIR model becomes increasingly pronounced. A comparison of baseline and GIIR models suggests that inclusion of geometric priors greatly facilitates extraction and fusion of the information from multi-view projections, leading to an improved image reconstruction.

Discussion

While deep learning has shown remarkable performance for image reconstruction, the existing data-driven methods rely totally on the inherent capability of deep learning to pin down the relationship between input and output data. The insight brought up here enables us to take advantage of unique properties of deep learning technique and geometry priors in image reconstruction. GIIR bridges the dimensionality gap between the 2D projection and 3D image domains via priors, which relieves the system from performing the non-trivial reasoning on the geometric relationship of the structures and allows the model to focus on learning semantic unknowns. Our results demonstrate the power of incorporating prior knowledge from physical geometry, specifically for the application of ultra-sparse reconstruction. Note that a key insight of integrating geometry priors with deep learning in the proposed GIIR framework is a general model-agnostic approach, which is not limited by the specific network configuration. Therefore, the approach is flexible, with 2D-Net and 3D-Net substitutable by other models of view-synthesis and image refinement. For example, the study in the novel-view X-ray projection synthesis could be applied here to benefit the reconstruction task.

In this study, the 3D CT image reconstruction approach with ultra-sparse sampling data is applied to lung CT image reconstruction. The approach is quite general and is extendable to other body sites, such as head and neck, abdomen, by using appropriate training datasets. Useful applications of the technique include longitudinal study (where prior high-quality image information is likely available) and image-guided interventions. For example, for applications in radiation therapy, the reconstructed volumetric image can be useful for guiding the patient setup with much reduced dose. For imaging of low-contrast structures, sampling with a higher view number may be needed to improve the detectability. Finally, the general insight of integrating geometry prior into deep learning is generalizable to a wide range of imaging systems such as PET and MRI, as will be demonstrated below in alternate embodiments.

MRI Implementation

In this embodiment, the invention provides a physics-aware deep learning framework for ultra-sparse magnetic resonance imaging.

This embodiment demonstrates a deep learning-based synthesis model to synthesize unacquired k-space samples from acquired data. It provides a physics-aware deep learning-based image reconstruction framework to reconstruct volumetric MRI from ultra-sparse k-space samples. It also provides a mechanism to integrate physics priors of the imaging process with the deep learning framework.

We investigate the problem of generating high quality volumetric MRI from ultra-sparse k-space samples that can be acquired within a second. Specifically, we propose a 2D-3D deep learning framework that consists of 3 modules: a) a 2D generation module that synthesizes 2D representations of unacquired k-space samples; b) a physics module that embeds both k-space encoding patterns and known relationships between k-space and image domains to unfold 2D representations to 3D volumetric space and c) a 3D refinement module that takes the unfolded 3D data and outputs high resolution volumetric images. The feasibility and potential impact of the physics-aware deep learning model are demonstrated using abdominal imaging cases. The proposed strategy is flexible with MRI acquisition schemes, including both Cartesian and radial acquisitions and provides a new paradigm for volumetric MRI acquisition with substantially reduced imaging time and cost.

Here we provide a strategy to integrate fixed priors of imaging physics with network-learned features for volumetric MRI reconstruction. Specifically, we introduce an effective physics module to bridge low-dimensional k-space samples and high dimensional volumetric images by utilizing known k-space sampling patterns and fixed transformations between k-space and image space. In volumetric MRI, sparse k-space samples form a low dimensional representation of the volumetric image space. The representation is determined by both imaging subject contents and k-space sampling patterns. The 2D generation module in the physics-aware deep learning framework synthesizes new representations associated with unacquired k-space samples, by exploring both shared content code between different representations (same imaging subject) and unique domain code of each representation (different k-space sampling geometry). The physics module then utilizes both known k-space sampling patterns and fixed transformations between k-space and image space to unfold 2D representations to 3D volumetric space. The 3D refinement module improves the resolution of the unfolded 3D data and outputs final high quality volumetric images. We demonstrate this physics-aware image reconstruction network can achieve an acceleration factor that permits real time acquisition of volumetric MRI, which may reform the current image guidance strategy for interventional procedures and significantly reduce the cost and time for many functional and quantitative imaging procedures.

This approach provides a feasible solution to generate volumetric MRI with sub-second data acquisition time without relying on surrogate signals. The physics-aware deep learning framework integrates fixed priors of imaging physics with network-learned features for volumetric MRI reconstruction that is robust to longitudinal patient changes and flexible with different acquisition schemes.

This implementation has applications to fast MRI with significantly reduced acquisition time and cost for simplified hardware design and clinical workflow. It can also be used for generation of volumetric images for real-time image-guided interventions, such as image-guided radiotherapy on a MR-Linac system. It also has application to generation of high temporal resolution image series to capture dynamic biological processes, such as diffusion-weighted MRI and dynamic contrast-enhanced MRI for more accurate disease diagnosis, clinical decision making and treatment planning.

The framework includes a 2D-3D deep learning network with an explicitly defined geometry module that embeds geometric priors of the k-space encoding pattern. A 2D generation network first augments the sparsely sampled image dataset by generating new 2D representations of the underlying 3D subject. A geometry module then unfolds the 2D representations to the volumetric space. Finally, a 3D refinement network takes the unfolded 3D data and outputs high-resolution volumetric images. Patient-specific models were trained for 7 abdominal patients to reconstruct volumetric MRI from both orthogonal cine slices and sparse radial samples. To evaluate the robustness of the proposed method to longitudinal patient anatomy and position changes, we tested the trained model on separate datasets acquired more than one month later and evaluated 3D target motion tracking accuracy using the model-reconstructed images by deforming a reference MRI with gross tumor volume (GTV) contours to a 5-min time series of both ground truth and model-reconstructed volumetric images with a temporal resolution of 340 ms. Incorporating geometric priors into deep learning model enables volumetric imaging with high spatial and temporal resolution, which is particularly valuable for 3D motion tracking and has the potential of greatly improving MRI-guided radiotherapy precision.

Introduction

In the present approach, a 2D and 3D deep learning networks are used with an explicitly defined geometry module that embeds both k-space sampling patterns and the known transform between k-space and image domain. Instead of creating volumetric images directly from k-space samples, which often suffers from severe artifacts due to extreme subsampling, we started our reconstruction by first enhancing 2D representations of the underlying 3D subject using a 2D generation network. The geometry module was then used to unfold the 2D representations to a volumetric space. Finally, a 3D refinement network took the unfolded 3D data and outputted high-resolution volumetric images. By simply changing the geometry module based on k-space sampling patterns, the same network structure was trained to reconstruct volumetric images from both cine MRI slices and sparse radial samples with sub-second acquisition time. To evaluate the robustness of the proposed method to longitudinal patient changes, we trained and tested the model on separate datasets acquired more than one month apart. The capability of the model-reconstructed images in support of 3D motion tracking was evaluated for 7 abdominal patients over a 5-min time period.

Materials and Methods

Problem Formulation

We investigated sparse sampling schemes for both cine and radial MRI. For cine MRI, interleaved acquisition was considered, which samples two orthogonal MRI slices of coronal and sagittal views respectively. For radial MRI, a stack-of-star acquisition pattern was used, where radial readout lines were acquired in the axial plane and Cartesian phase encoding was performed in the superior-inferior direction. The sequence sampled all radial lines with the same angle throughout the superior-inferior direction before moving to the next radial angle. A collection of radial lines with the same angle forms a radial spoke. In our study, we sampled two radial spokes with radial angles of $0°$ and $111.25°$ (the golden angle) respectively. Inverse Fourier transforming each of the 2 radial spokes gives 2 projection images of the patient. Both acquisition schemes take less than 1 second (about 500 ms for orthogonal cine acquisition and 340 ms for radial acquisition) for large field-of-view imaging such as abdominal MRI.

With the ultra-sparse sampling scheme, filling out missing data samples in the volumetric space directly is challenging. Instead, we formulated a 2D data completion problem first before reconstructing 3D volumetric images. Denote the underlying volumetric image with an image size of $M \times M \times K$ as $I \in \mathbb{R}^{M \times M \times K}$, for cine acquisition, we constructed 2D representations of the 3D subject by sampling rotating planar images from the volumetric image. The sampling coordinates were defined in the cylindrical coordinate system with origin at the volume center and longitudinal axis parallel to the superior-inferior direction of the volume. Under this coordinate system, sampling locations for the acquired coronal cine slice $p_0 \in \mathbb{R}^{M \times K}$ were $$\left\{ \rho, \theta, z \mid \rho = 1, 2, \cdots, \frac{M}{2}; \theta = 0, \pi; z = -\frac{K}{2}, \cdots, \frac{K}{2} \right\}$$

and the sampling locations for the sagittal slice $p_1 \in \mathbb{R}^{M \times K}$ were similarly defined with $\theta = \{\pi/2, 3\pi/2\}$. With the two acquired slices, the goal is to complete n rotating slices $p_2, \ldots, p_{n+1}$ sampled with $\theta = \{\pi(i-1)/2n, 3\pi(i-1)/2n\}$ for slice $p_i$. For radial acquisition, 2D representations were similarly constructed by sampling the k-space with varying radial angles and performing inverse Fourier transform of radial spokes to generate projection images. Denote the projection images generated with acquired radial spokes as $p_0 \in \mathbb{R}^{M \times K}$ and $p_1 \in \mathbb{R}^{M \times K}$, we aim to complete n more projection images $p_2, \ldots, p_{n+1}$ that correspond to radial spokes with radial angle equals $i \times 111.25°$ for projection $p_i$.

After defining the target 2D representations, a 2D generation network $\Phi_i$ with network weights $W_1$ was trained to complete missing data in 2D space by synthesizing target 2D representations from acquired 2D samples $\Phi_1(p_0, p_1; W_1) = (p_0, p_1, \hat{p}_2, \ldots, \hat{p}_{n+1})$ A geometry module $\Phi_2$ with fixed weights $W_2$ then unfolded both acquired and network-generated 2D representations to the volumetric space $\Phi_2(p_0, p_1, \hat{p}_2, \ldots, \hat{p}_{1+1}; W_2) = \hat{I} \in \mathbb{R}^{M \times M \times K}$. Finally, a 3D refinement network $\Phi_3$ with learnt weights $W_3$ took the unfolded volumetric data from the geometric module as input and outputted final reconstructed images $\Phi_3(\hat{I}; W_3) = I_{recon} \in \mathbb{R}^{M \times M \times K}$. In this study we set n=10. FIG. 9 presents the framework of the geometry-informed deep learning model, and the following sections describe each model component in detail.

Figures 9A, 9B, 9C:
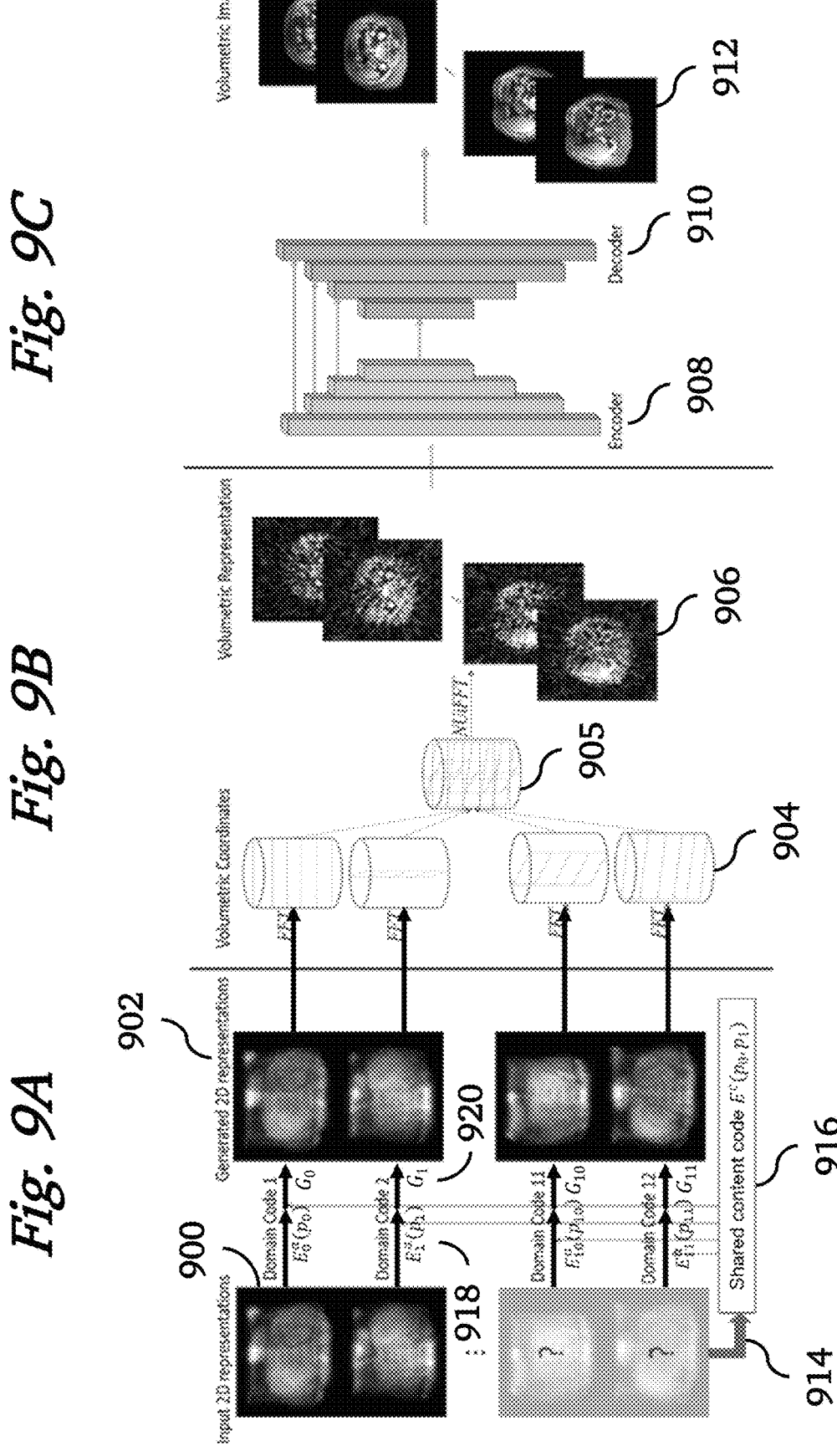
FIGS. 9A-9C. Three modules of the proposed deep learning framework (with radial MRI as an example).

FIGS. 9A-9C illustrate the processing pipeline using three modules of the deep learning framework (with radial MRI as an example). FIG. 9A shows a 2D generation network that synthesizes from sparse input 2D representations 900 new 2D representations 902 associated with unacquired k-space samples. FIG. 9B illustrates a geometry module that uses both sampling pattern and known k-space-to-image domain transforms to generate from 2D representations 902 volumetric coordinate data 904 and then to generate volumetric representations 904. FIG. 9C shows a 3D refinement network including an encoder 908 and decoder 910 that refines image quality of the volumetric representations 906 to produce final volumetric images 912.

Model Architecture

2D Generation Network

Similar to the above embodiment for sparse-view computed tomography reconstruction shown in FIG. 3, here FIG. 9A shows a multi-domain image translation model synthesizes new 2D representations 902 from acquired 2D representations 900. The domain translation/view synthesis model has the same model structure as in FIG. 3 while just changing the CT 2D projections to MRI 2D representations. The model views each 2D representation as a separate domain and completes missing domain information by exploiting both shared content between different domains (same patient anatomy) and unique information associated with each domain (different sampling locations). The network includes 1) a shared content encoder $E^c$ 914 that encodes information shared by different representations into a content code c 916; 2) domain-specific encoders $$E_i^a$$

918 that encode unique information of different representations into domain-specific codes $a_i$, i=0,1, . . . n+1; 3) generators $G_i$ 920 that generate new representations by combining shared content code c and domain specific codes $a_i$, i=0,1, . . . n+1 and 4) discriminators $D_i$, i=0,1, . . . n+1 that distinguish generated representations and real representations. The network was trained by optimizing the total loss including the reconstruction loss, the adversarial loss and the cycle consistent loss $$\min_{E^c, E_i^a, G_i} \max_{D_i} \sum_{i=0}^{1} L_{cyc}^{p_i} + L_{cyc}^c + \sum_{i=0}^{n+1} \left( L_{cyc}^{a_i} + L_{adv}^{p_i} + L_{rec}^{p_i} \right) \quad (1)$$

where $L_{cyc}$ is the L1-norm cycle-consistent loss including representation consistency loss that enforces synthesized 2D representations to be consistent with input representations (planar images or projections), which is optimized over the 2 acquired representations.

$$L_{cyc}^{p_i} = \|G_i(E^c(p_0, p_1), E_i^a(p_i)) - p_i\|_1, i = 0, 1 \quad (2)$$

and coding consistency loss that enforces consistency of both shared content code and domain-specific codes before decoding and after encoding.

$$L_{cyc}^c = \|E^c(G_0(c, a_0), \ldots, G_{n+1}(c, a_{n+1})) - c\|_1 \quad (3)$$

-continued $$L_{cyc}^{a_i} = \|E_i^a(G_i(c, a_i)) - a_i\|_1, \ i = 0, 1, \ldots n + 1 \qquad (4)$$

We assume prior distribution for the domain-specific codes $a_i$ is a standard Gaussian distribution $\mathcal{N}$ (0, I). During image generation, the generator samples domain-specific codes from the prior distribution and combines the domain-specific codes with the shared content code to synthesize 2D representations. $L_{adv}$ and $L_{rec}$ are the adversarial loss and L1-norm reconstruction loss respectively.

$$L_{adv}^{p_i} = \log(1 - D_i(G_i(c, a_i))) + \log(D_i(p_i)), \ i = 0, 1, \ldots n + 1 \qquad (5)$$

$$L_{rec}^{p_i} = \|G_i(c, a_i) - p_i\|_1, \ i = 0, 1, \ldots n + 1$$

Geometry Module

As shown in FIG. 9B, a geometry module was defined for cine and radial MRI. The geometry module is deterministic for given a sampling pattern and requires no additional training. For cine MRI, the geometry module populates voxel information of the 3D volume based on volumetric sampling coordinates of both acquired orthogonal cine slices and network-synthesized rotating planar images. Specifically, the geometry module estimates the voxel intensity at $$(m, n, k), -\frac{M}{2} < m, n \le \frac{M}{2}, -\frac{K}{2} < k \le \frac{K}{2},$$

as $$\hat{I}(m,n,k) = \hat{I}(r;\theta,k) = w_{1,1} p_i(r_1,k) + w_{2,1} p_j(r_1,k) + w_{1,2} p_i(r_2, k) + w_{2,2} p_j(r_2,k) \qquad (7)$$

where $r = \sqrt{m_2 + n_2}$ and $$\theta = \cos^{-1}\left(\frac{m}{r}\right)$$

are the cylindrical coordinates of the target voxel. $p_i$ and $p_j$ are the two rotating planar images with sampling coordinates $\theta_i \le \theta \le \theta_j$. The geometry module performs a bilinear interpolation using pixel information from $p_i$ and $p_j$ at location $(r_1, k)$ and $(r_2, k)$ with $r_1 \le r \le r_2$ and $w_{11}, \ldots w_{22}$ are the interpolation weights, determined based on the distance between the interpolation locations and the sampled locations.

For radial MRI, the geometry module first performs a 2D uniform Fourier transform on each of the projection images 902 to get the corresponding radial spokes $\mathcal{F}(p_i) = P_i$, $i = 0, 1, \ldots, n+1$ 904 and fills out the volumetric k-space based on both acquired and network-synthesized radial samples $\mathcal{F}(p_i)$ 905. A non-uniform 3D Fourier transform (3DNUFFT) is then performed on the volumetric k-space data 905 to reconstruct 3D images 906. As the radial sampling pattern leads to a denser sampling of the k-space center than the periphery, a p filter was used to compensate for the difference in sampling density in k-space before 3D NUFFT. Specifically, the filter multiplies k-space samples at sampling location $v = (k_x, k_y, k_z)$ with density compensation weights $w(v) = w_0(v) e^{-2\pi\sigma^2\|v\|^2}$, where $w_0(v)$ equals the k-space volume of a semicylindrical shell with central radius $|v'|$. The shell height and width equal to the sample spacing in the longitudinal and radial directions, respectively. To reduce ringing, a Gaussian window with $\sigma = 1$ voxel was also included in the density compensation function.

Volumetric Refinement Network

The 3D images 906 created by the geometry module is generally not perfect and may contain imaging artifacts due to sparse sampling. As shown in FIG. 9C, a 3D network was used to refine the quality of volumetric images 906. A U-Net based encoder-decoder network was built, where the encoder 908 has four-stage down-sampling blocks and the decoder 910 has four-stage up-sampling blocks. Similar with previously described embodiment on CT reconstruction, each down-sampling and up-sampling block has double 3D convolution layers followed by rectified linear unit activation layers and group normalization layers. The down sampling operation was implemented by a max pooling layer with a step of (2,2,2) and up sampling was implemented by interpolation. Hierarchical skip connections were built by concatenating feature maps between encoder and decoder of the same feature level. A final 3D convolution layer with kernel size of 1×1×1 and hyperbolic tangent activation function was used to output the reconstructed 3D image 912. The network was trained by minimizing the L1-norm difference between network outputs and the ground truth.

Model Training and Evaluation

Data from seven patients with intrahepatic tumors was collected. A patient-specific deep learning model was trained separately for each of the seven patients using a 4D MRI dataset of 21 breathing motion phases. The 4D MRI was acquired with a golden-angle stack-of-stars spoiled gradient echo sequence and reconstructed through retrospective k-space sorting and re-binning using a previously published technique. All MRI data were acquired using a 3 Tesla scanner (Skyra, Siemens Medical Systems, Erlangen, Germany) with an 18-channel flexible surface coil (BodyMatrix) placed anteriorly and 1 or more posterior 4-channel coils embedded in the patient couch (Spine Matrix). The field of view covered the liver, stomach and a large portion of the intestines. The imaging parameters ranged from 1.14 to 1.21 ms for echo time, 2.71 to 4.51 ms for repetition time, 10° to 14° for flip angle, 2 to 2.45 mm for in-plane voxel size and 3 to 4 mm for slice thickness. The size of the imaging matrix was 192×192 and the number of slices was 64.

The training dataset was augmented by applying 3D deformations to volumetric MR images. To generate new deformation fields, principal component analysis (PCA) was performed on deformation fields associated with each of the 21 MR images that align the exhale phase MR image to other breathing motion phases, which were extracted in previous studies using B-spline deformable registration. New deformation fields were generated using the mean PC mode $m_0$ and the leading 3 PC modes $m_1$, $m_2$, $m_3$ as $d = m_0 + \alpha_1 m_1 + \alpha_2 m_2 + \alpha_3 m_3$ where a was varied between ±3 standard deviation around the mean PC coefficients. Through this data augmentation process, we obtained a total number of 2500 volumetric images, where 2400 images were randomly selected for training purpose and the remaining for validation purpose.

All MR images were then normalized to an intensity range of [0,1]. To train the 2D generation network, the volumetric MR images were retrospectively subsampled to 2 orthogonal cine slices or 2 radial projection images, which served as the model input. After the 2D training was completed, the geometry module was used to generate volumetric images from the network-predicted 12 rotating planar images or 12 projection images. The geometry module-generated volumetric images were then paired with ground truth images to train the 3D refinement network. Both 2D and 3D networks were trained using an Adam optimizer and a batch size of 1. The learning rate and number of iterations were 0.001/0.005 and 50000/30000 for 2D and 3D training respectively. Random 3D translation and rotation were also applied to MR images before each training epoch. To evaluate the impact of incorporating geometric priors, we compared the proposed model to a baseline deep learning model that is purely data-driven. The baseline model consists of a 2D encoder and a 3D generator with a feature transformation module that connects 2D and 3D feature space. We trained the baseline model using the same dataset of paired 2D slices/projections and 3D images as the proposed model.

To evaluate the robustness of the trained model to longitudinal patient anatomy and position changes during a radiotherapy course, we applied the trained model to a testing dataset that was acquired more than one month after the training dataset. The same imaging sequence and parameters were used. A 5-min time series of dynamic MRI was reconstructed from the acquired k-space samples with a temporal sampling rate of 340 ms. The reconstruction was based on a previously published technique for high temporal and spatial resolution breathing motion characterization via retrospective motion state labeling and served as the ground truth for model evaluation. We subsampled the ground truth volumetric images to 2 orthogonal slices or 2 projections images and input the sparse samples to the trained model. The model-reconstructed volumetric images were compared to the ground truth images in support of 3D abdominal target tracking. Specifically, the first image of the ground truth image time series was chosen as the reference image with clinically defined gross tumor volume (GTV) contours transferred to it. The reference image was then deformed to match both ground truth and model-reconstructed volumetric images using B-spline deformable registration implemented in NiftyReg, a registration method which has been validated in previous studies for aligning different breathing motion states. Target motion during the 5-min time period was characterized by deforming the reference GTV volume with calculated deformation fields. Tracking accuracy using model-reconstructed volumetric images was evaluated by calculating the difference between centroid positions of deformed GTV volumes and 95-percentile Haursdorff distance between deformed GTV contours. The linear correlation of motion estimation using model-reconstructed images and ground truth images was also assessed similarly with previous work, where linear fitting was performed between the ground truth and model-estimated GTV centroid displacements in the superior-inferior direction and the R-square value was calculated.

Results

Model Validation

Figure 10A:
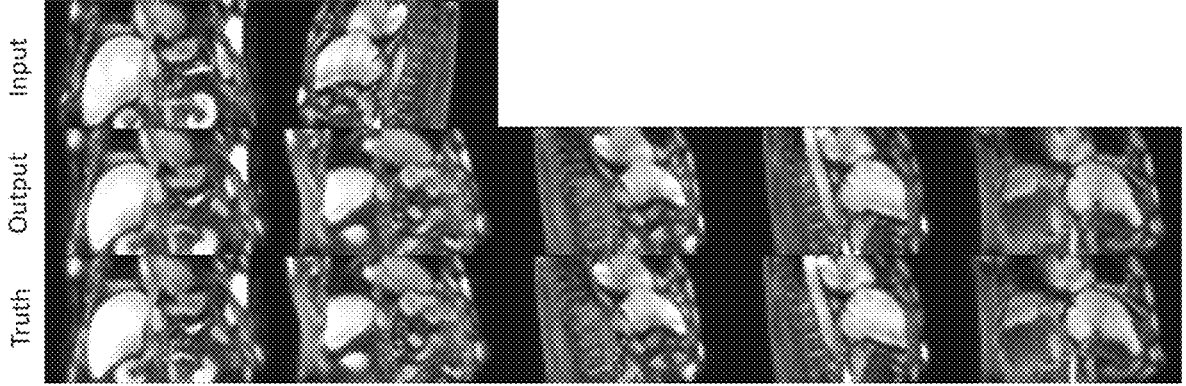
FIG. 10A. Example network-predicted rotating planar images from 2 orthogonal cine slices.
Figure 10B:
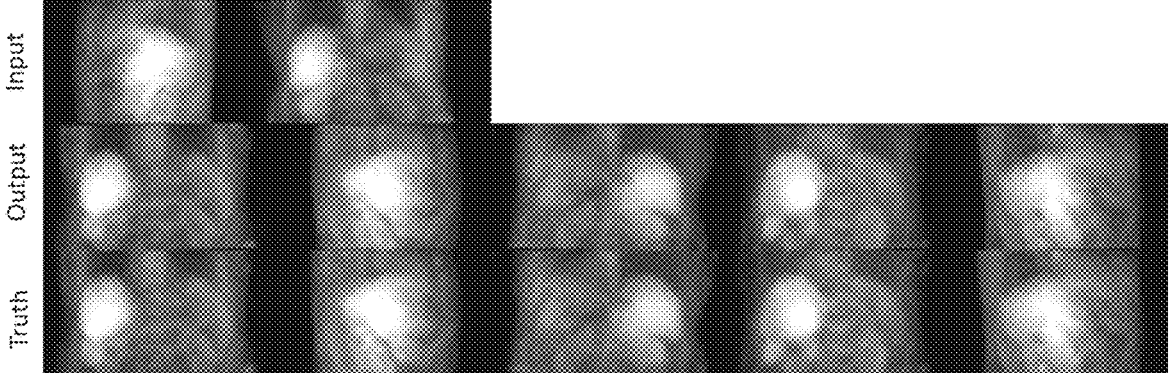
FIG. 10B. Example network-predicted radial projections from 2 radial projections.
Figure 11A:
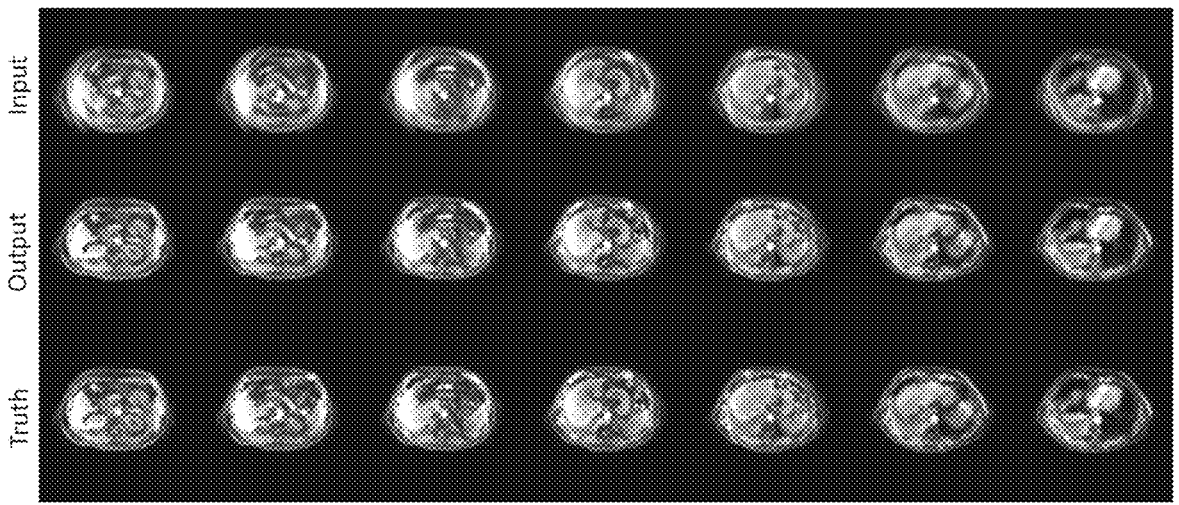
FIG. 11A. Sample slices of volumetric input generated from the geometry module and output generated from the 3D refinement network for cine acquisition.
Figure 11B:
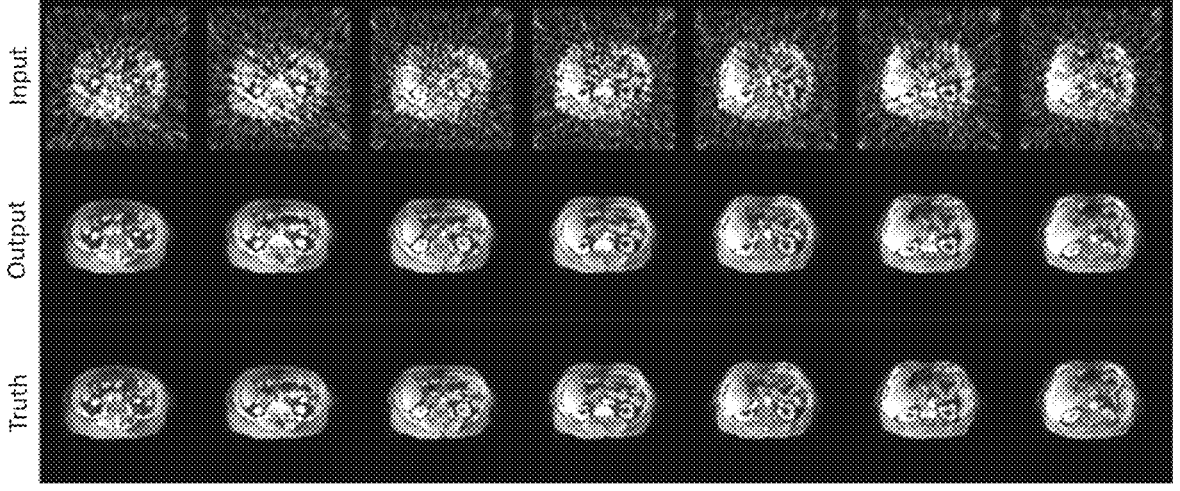
FIG. 11B. Sample slices of volumetric input generated from the geometry module and output generated from the 3D refinement network for radial acquisition.

After the model training, generating one volumetric MRI from sparse samples took 8.8 ms using a Nvidia Tesla K40C GPU. FIGS. 10A, 10B show example model validation results for the 2D generation network. The trained network is able to synthesize new 2D representations that closely match the ground truth from both cine and radial acquisitions. FIGS. 11A, 11B show volumetric images produced by the geometry module, which serve as the input to the 3D refinement network and the final network-reconstructed volumetric images. Table 2 summarizes quantitative evaluation results including structural similarity index (SSIM), peak signal-to-noise ratio (PSNR) and mean square error between the network reconstruction and the ground truth.

TABLE 2

| Quantitative evaluation of reconstructed image quality across 7 patients | | | |
|---|---|---|---|
| Acquisition/ Reconstruction Scheme | SSIM | PSNR | MSE |
| Cine/Proposed | 0.85 ± 0.05 | 25.1 ± 2.1 | 0.004 ± 0.001 |
| Cine/Baseline | 0.75 ± 0.04 | 23.5 ± 1.8 | 0.005 ± 0.002 |
| Radial/Proposed | 0.85 ± 0.05 | 25.1 ± 2.4 | 0.004 ± 0.002 |
| Radial/Baseline | 0.75 ± 0.06 | 23.5 ± 2.0 | 0.005 ± 0.003 |

Figure 12:
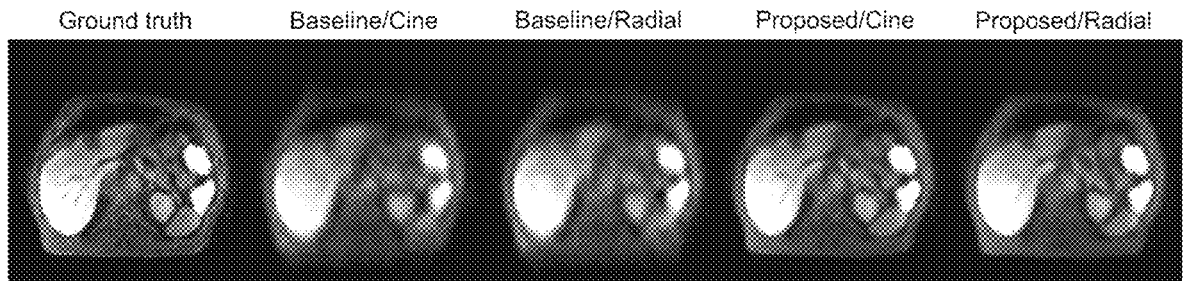
FIG. 12. Sample slices of volumetric images reconstructed using the baseline model and the proposed model respectively, with cine slices and radial projections as inputs.

FIG. 12 compares sample slices of 3D images reconstructed by the proposed model and the baseline model. The proposed model reduces blurry artifacts and outperforms the baseline model in terms of various image quality metrics, including structural similarity index (SSIM), peak signal-to-noise ratio (PSNR) and mean square error between model reconstruction and ground truth, as summarized in Table 2.

Volumetric Target Tracking

Figure 13:
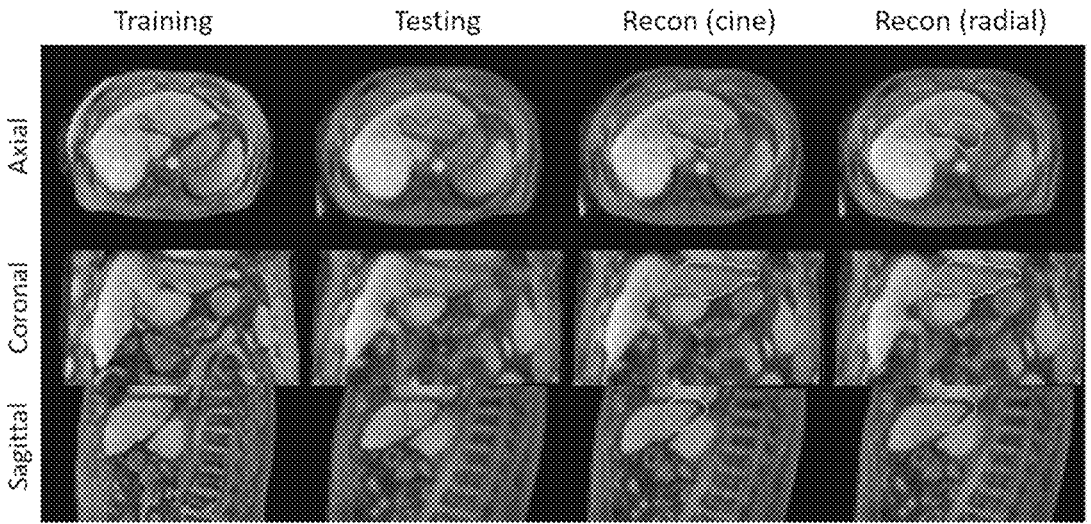
FIG. 13. Sample views of training, testing and model-reconstructed MRI images. Red and green contours show GTV volume defined by deforming a reference image to testing and model-reconstructed images respectively.
Figure 14:
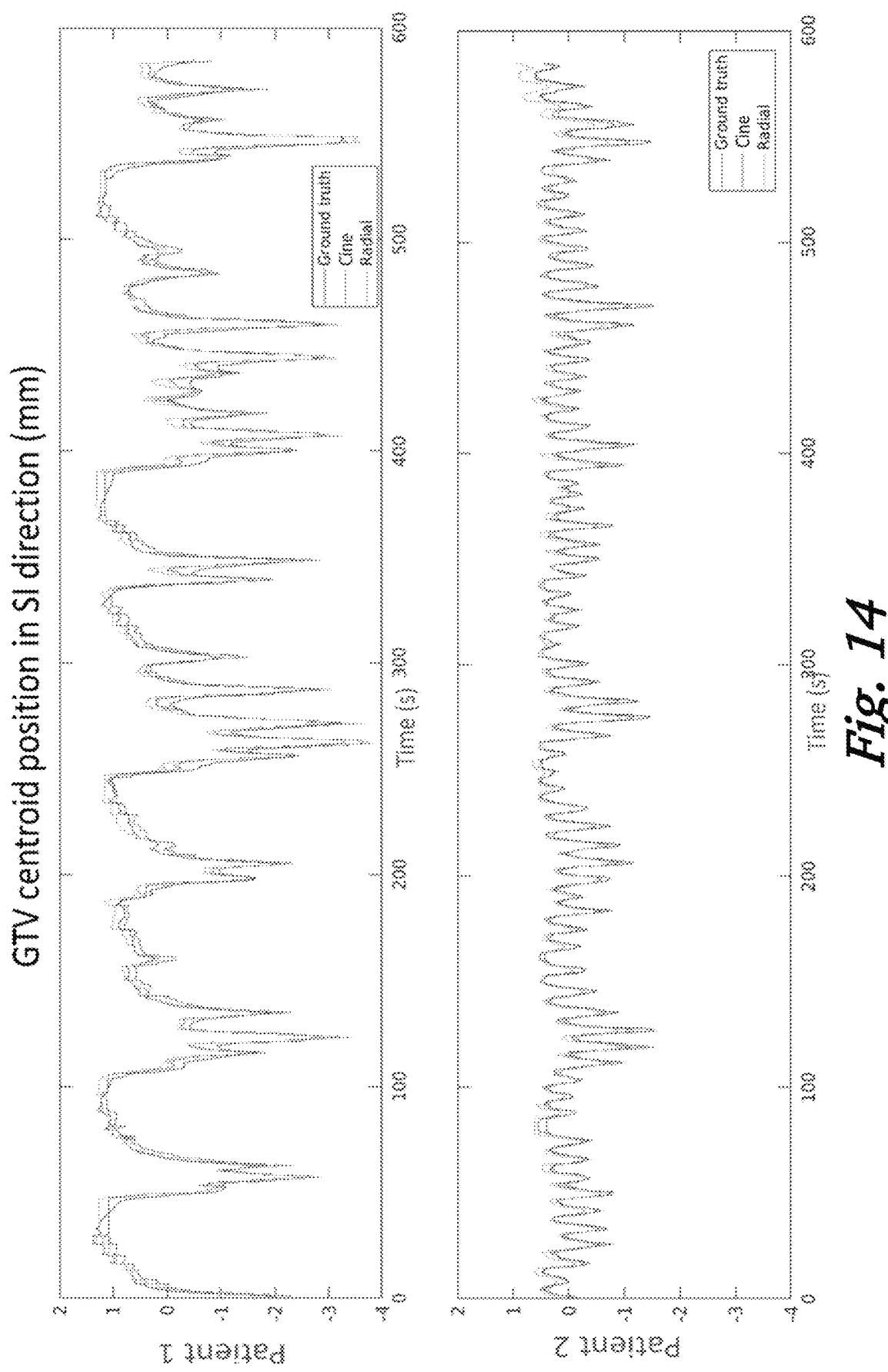
FIG. 14. Example motion traces of GTV centroid in superior-inferior direction.

FIG. 13 shows sample views of training and testing volumetric MRI. Positional and anatomical changes can be observed in all planes due to long acquisition time intervals between the training and testing datasets, while network-reconstructed images show good agreement with testing images. FIG. 14 plots example motion traces of gross tumor volume (GTV) centroid in the superior-inferior direction during the 5-min examination. Despite of varying motion patterns and motion irregularities across patients, the motion traces estimated using the model-reconstructed volumetric images are consistent with the ground truth. Across the 7 patients evaluated, the motion was most significant in the superior-inferior (SI) direction. The median distances between GTV centroids during the 5-min period and the reference GTV centroid ranged between 0.4 mm to 2.6 mm in the SI direction. The median distances in the left-right (LR) and anterior-posterior (AP) direction were less than 1 mm for most patients except for one patient where the distance was 1.4 mm in the AP direction. By updating the reference GTV centroid position using model-reconstructed volumetric images, the median distances in the SI direction were reduced and were less than 1 mm for all patients evaluated. Table 3 summarizes the differences in GTV centroid position estimation using ground truth and model-reconstructed images. The GTV contour agreement, evaluated as 95-percentile Hausdorff distance between predicted and ground truth GTV contours were 4.7±1.1 mm and 3.2±1.5 mm for cine and radial acquisitions respectively, which is of the same scale as cross-plane imaging resolution (3.5~4 mm).

TABLE 3

| Median distances between predicted and ground truth GTV centroid positions across patients | | | |
|---|---|---|---|
| Acquisition scheme | AP | LR | SI |
| Cine | 1.1 ± 0.5 mm | 1.0 ± 0.5 mm | 0.4 ± 0.3 mm |
| Radial | 1.2 ± 0.6 mm | 0.5 ± 0.5 mm | 0.5 ± 0.4 mm |

The model-estimated GTV centroid displacements showed excellent linear correlation with the ground truth, with an R-square of 0.99, as comparing to the previously reported R-square of 0.95. It is also worth noting the model was tested on datasets that exhibit longitudinal anatomical changes from the training dataset, as opposed to training and testing using images acquired in the same imaging session.

The robustness of the proposed method to longitudinal changes may remove the need of acquiring 4D MRI before each treatment session and has the potential of supporting a simplified clinical workflow.

Discussion

A geometry-informed deep learning model for volumetric MRI reconstruction with ultra-sparse k-space sampling is described. The technique makes it possible to obtain volumetric MRI images with sub-second acquisition time, which is highly desirable for real time 3D motion tracking during MRI-guided interventions. To regularize the ill-posed problem of image reconstruction from sparse samples, both patient-specific priors learnt by the deep neural network and geometric priors that are inherent to the imaging system were exploited, which is different from previous deep learning-based image reconstruction strategies that are purely data-driven. The proposed deep learning framework uses a 2D generation network that completes subsampled image dataset in 2D space, a geometry module that bridges the gap between 2D and 3D space, and a 3D refinement network that reconstructs final volumetric images. By simply changing the geometry module based on pre-defined acquisition schemes, the same network structure can be trained to reconstruct volumetric MRI from both cine and radial samples. The trained model was evaluated for seven abdominal patients in support of 3D target tracking during a 5-min time period. The median distances between the GTV centroid positions predicted by the model and derived from the ground truth in the superior-inferior direction were less than 1 mm on average and around 1 mm in the other two directions, for both cine and radial acquisitions.

While consistency of model estimation with acquired data at sampled k-space locations has been utilized to constrain the image reconstruction process, the geometry of encoding an image subject into Fourier samples at different k-space locations has not been fully exploited. In this study, we introduced a network that generates new 2D representations based on known spatial encoding patterns of different representations (e.g., different planar or radial angles) and a geometry module that bridges the 2D representations and 3D images based on the sampling geometry and known transform between k-space and image space. Incorporating such geometric prior that is deterministic with the imaging system leverages the learning task of deep neural network and permits image reconstruction from ultra-sparse k-space samplings with sub second acquisition time. Furthermore, both network-learned and geometric priors are not bound to a specific imaging session or acquisition position, which makes the method desirable for real time imaging guidance over an entire radiotherapy course that is delivered over multiple days, as demonstrated by testing the model on separate datasets acquired more than one month later than the training dataset.

CONCLUSION

In this embodiment, a geometry-informed deep learning model that reconstructs volumetric MRI from ultra-sparse k-space samples has been described. It has applications to real time 3D motion tracking during MRI-guided radiotherapy. By exploiting geometric priors that are inherent to the imaging system, the learning task of the neural network is simplified and can be focused on learning patient-specific priors. Model-reconstructed volumetric MRI from both cine and radial samples with sub-second acquisition time shows sufficient accuracy in tracking 3D abdominal target motion. Furthermore, we demonstrated the robustness of the trained model to patient position and anatomy changes over time by testing the model using a longitudinal dataset, which makes the proposed method desirable for providing imaging guidance during a radiotherapy course that is fractionated over multiple days.

The invention claimed is:

1. A method for medical imaging comprising:
performing a sparse-sampled tomographic imaging acquisition by an imaging system to produce acquired sparse imaging samples;
synthesizing by a first deep learning network unacquired imaging samples from the acquired imaging samples to produce complete imaging samples comprising both the acquired imaging samples and unacquired imaging samples;
transforming by a physics module the complete imaging samples to image space data based on physics and geometry priors of the imaging system;
wherein the physics and geometry priors of the imaging system comprise geometric priors of a physical imaging model of the imaging system, and prior geometric relationships between the sample and image data domains;
performing image refinement by a second deep learning network to produce tomographic images from the image space data.

2. The method of claim 1 wherein the imaging system is a CT imaging system.

3. The method of claim 1 wherein the synthesized unacquired imaging samples are novel-view projections of the CT imaging system.

4. The method of claim 1 wherein the physics model comprises a geometric back-projection operator to transform 2D projections to 3D images based on known geometric properties of the imaging system.

5. The method of claim 1 wherein the imaging system is an MRI imaging system.

6. The method of claim 1 wherein the synthesized unacquired imaging samples are k-space samples of the MRI imaging system.

7. The method of claim 1 wherein the physics module comprises a physics-aware image reconstruction framework trained to reconstruct volumetric MRI images from ultra-sparse k-space samples based on both known k-space sampling patterns and fixed transformations between k-space and image space.

8. The method of claim 1 wherein the physics module transforms k-space samples to volumetric images by using known k-space sampling patterns of the MRI imaging system and fixed transformations of the MRI imaging system between k- space and image space.

* * * * *